United States Patent [19]
Kriesel

[11] Patent Number: 5,569,236
[45] Date of Patent: Oct. 29, 1996

[54] FLUID DELIVERY APPARATUS

[75] Inventor: Marshall S. Kriesel, St. Paul, Minn.

[73] Assignee: Science Incorporated, Bloomington, Minn.

[21] Appl. No.: 269,445

[22] Filed: Jun. 30, 1994

Related U.S. Application Data

[63] Continuation-in-part of Ser. No. 129,470, Sep. 29, 1993, Pat. No. 5,374,256, which is a continuation-in-part of Ser. No. 129,693, Sep. 29, 1993, Pat. No. 5,419,771, which is a continuation-in-part of Ser. No. 69,937, May 28, 1993, Pat. No. 5,336,188, which is a continuation-in-part of Ser. No. 46,438, May 18, 1993, Pat. No. 5,411,480, which is a continuation-in-part of Ser. No. 987,021, Dec. 7, 1992, Pat. No. 5,279,558, which is a continuation of Ser. No. 870,269, Apr. 17, 1992, Pat. No. 5,205,820, which is a continuation-in-part of Ser. No. 642,208, Jan. 16, 1991, Pat. No. 5,169,389, which is a continuation-in-part of Ser. No. 367,304, Jun. 16, 1989, Pat. No. 5,019,047.

[51] Int. Cl.$^6$ .................................................... A61B 19/00
[52] U.S. Cl. ........................ 604/403; 604/406; 604/189; 604/236
[58] Field of Search ................................ 604/83, 87, 89, 604/187, 189–190, 201, 203, 232–236, 403, 405, 406, 415, 230; 128/760, 763, 764, 766, 767

[56] References Cited

U.S. PATENT DOCUMENTS

| | | | |
|---|---|---|---|
| 3,862,042 | 1/1975 | Ayres | 604/190 X |
| 3,875,012 | 4/1975 | Dorn et al. | 604/415 X |
| 4,048,997 | 9/1977 | Raghavachari et al. | 604/189 |
| 5,338,312 | 8/1994 | Montgomery | 604/230 |

*Primary Examiner*—Corrine M. McDermott
*Attorney, Agent, or Firm*—James E. Brunton

[57] ABSTRACT

A fluid container assembly which can be aseptically filled in the field with selected fluids and one which is specially designed for sterile coupling and use with fluid dispensing and delivery devices of the character that embody stored energy sources such as compressible cellular masses and distendible elastomeric membranes that form, in conjunction with a cooperating base, fluid chambers for containing the fluid to be dispensed.

14 Claims, 21 Drawing Sheets

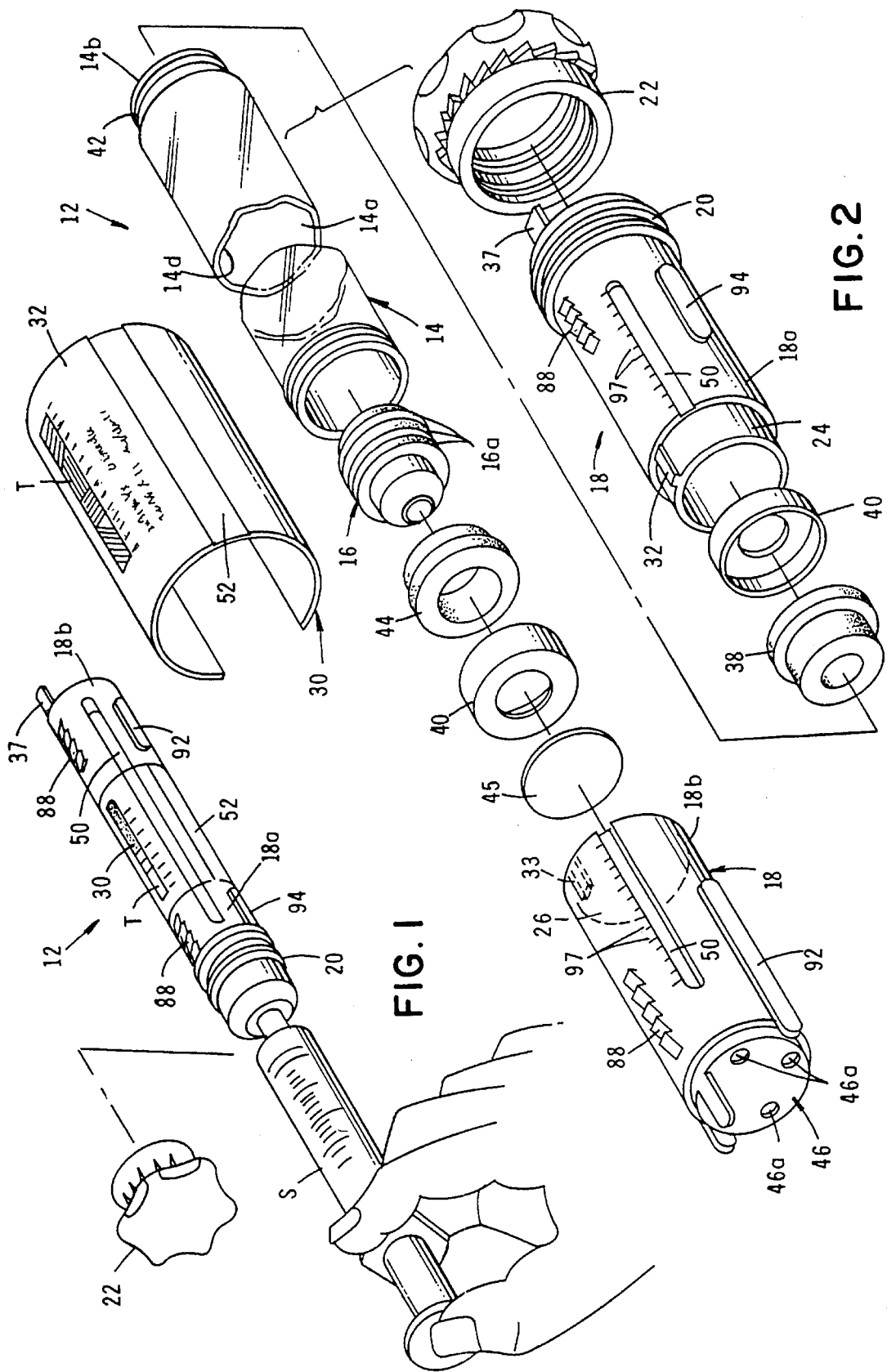

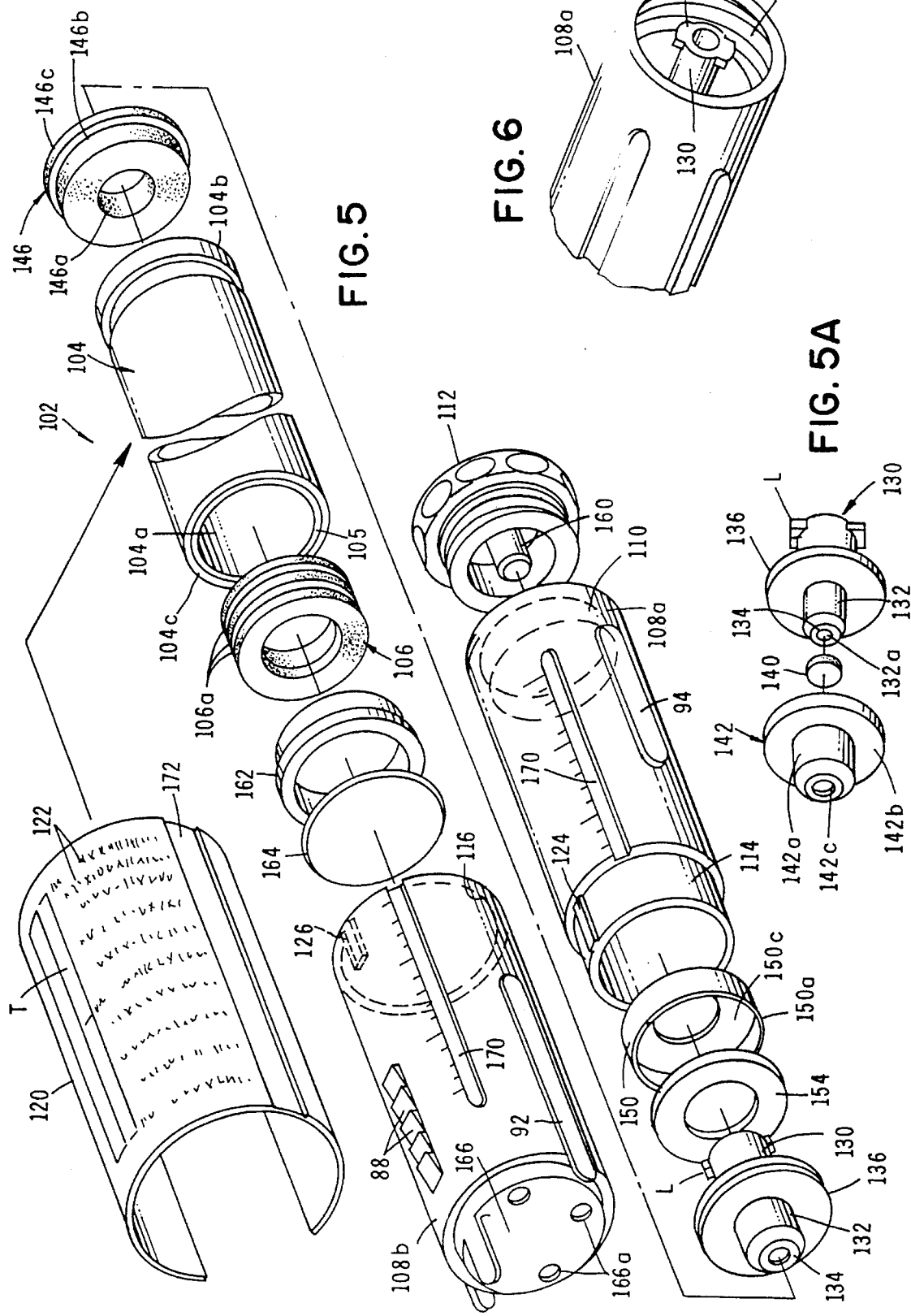

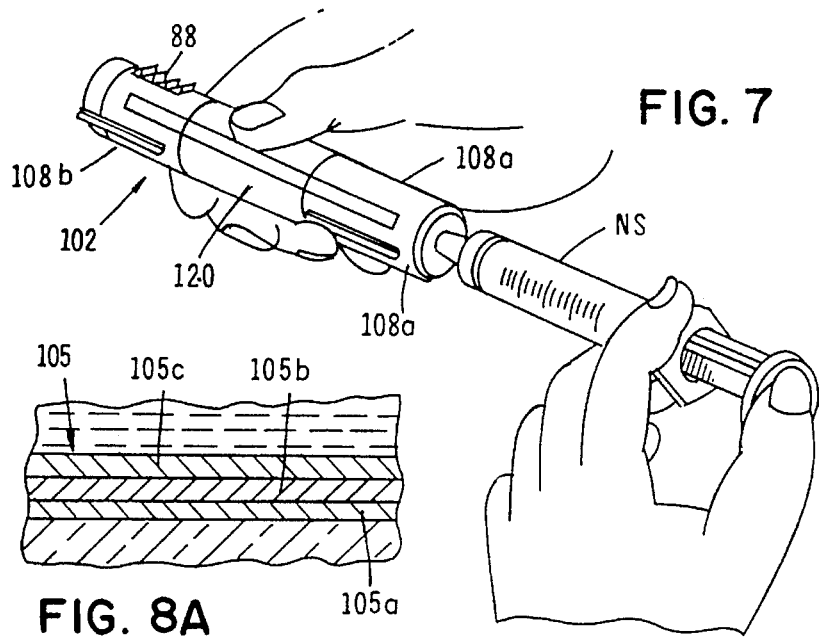
FIG. 7
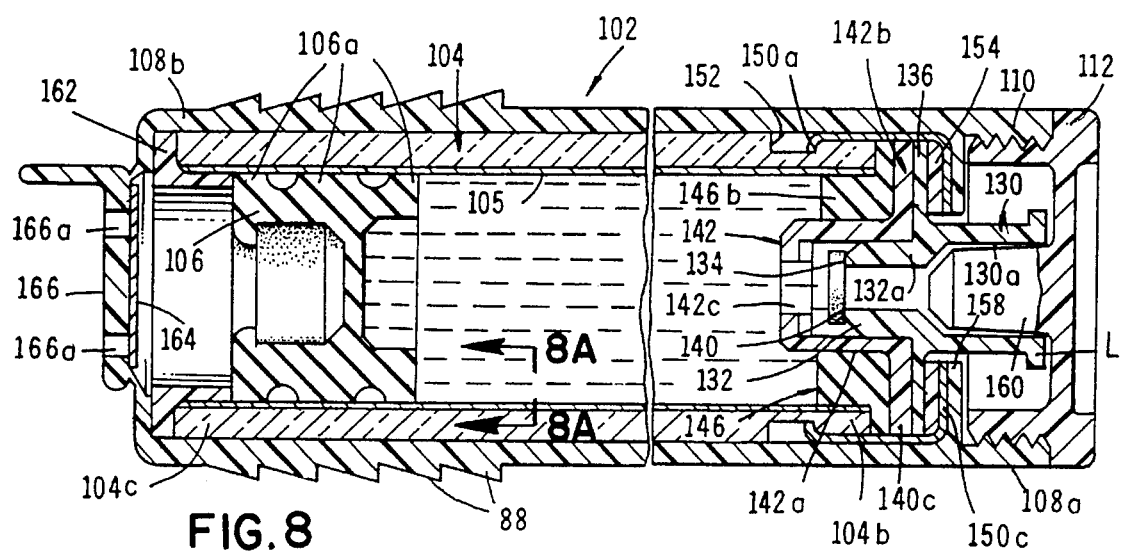
FIG. 8A
FIG. 8
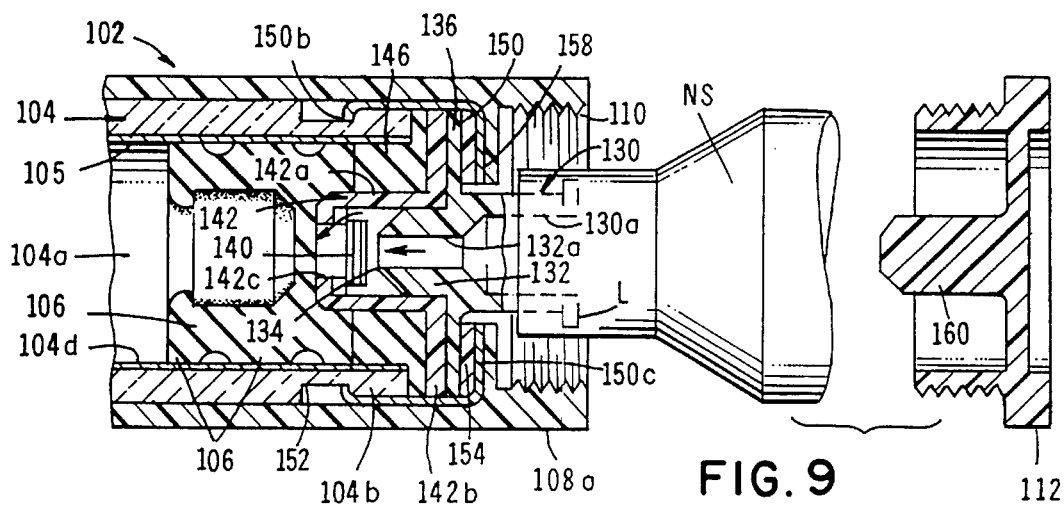
FIG. 9

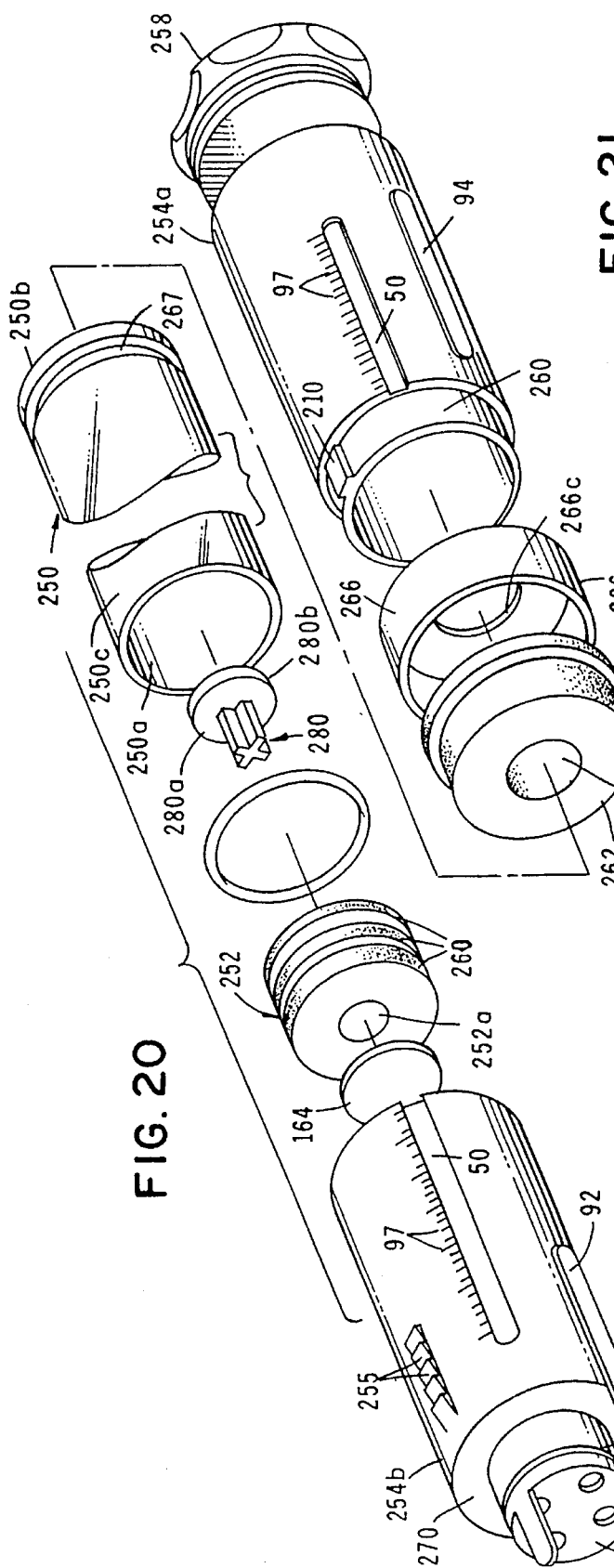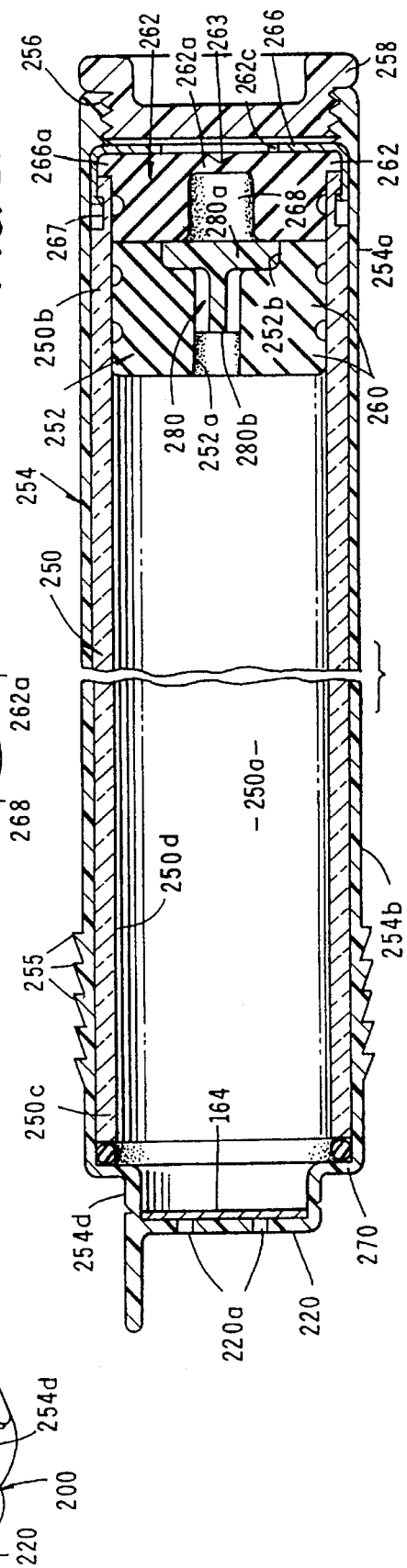

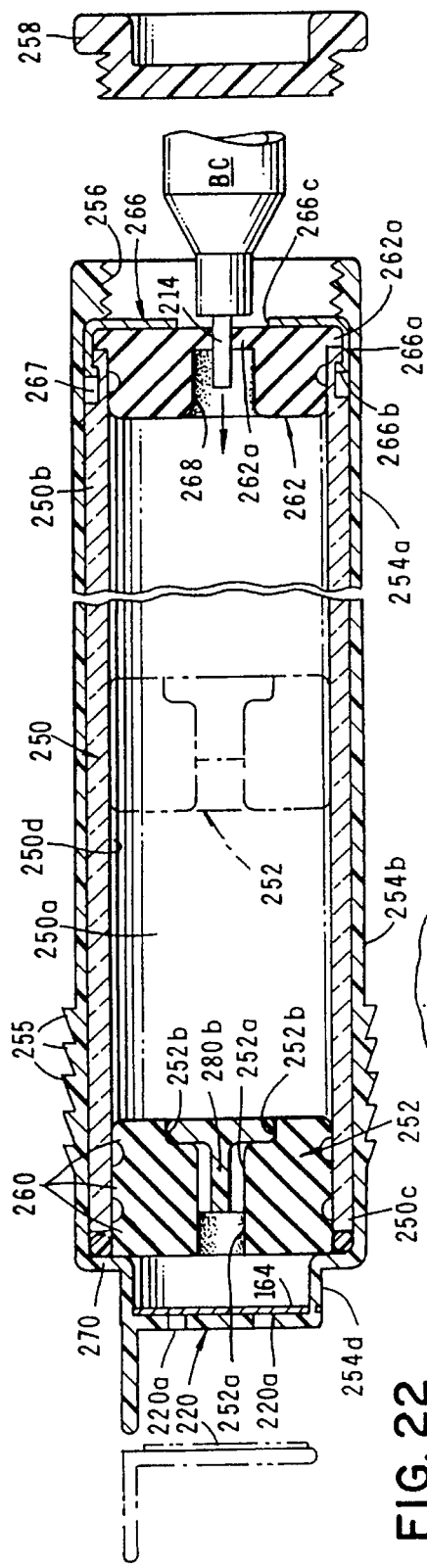
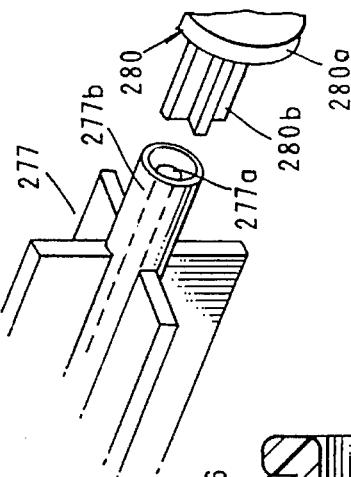
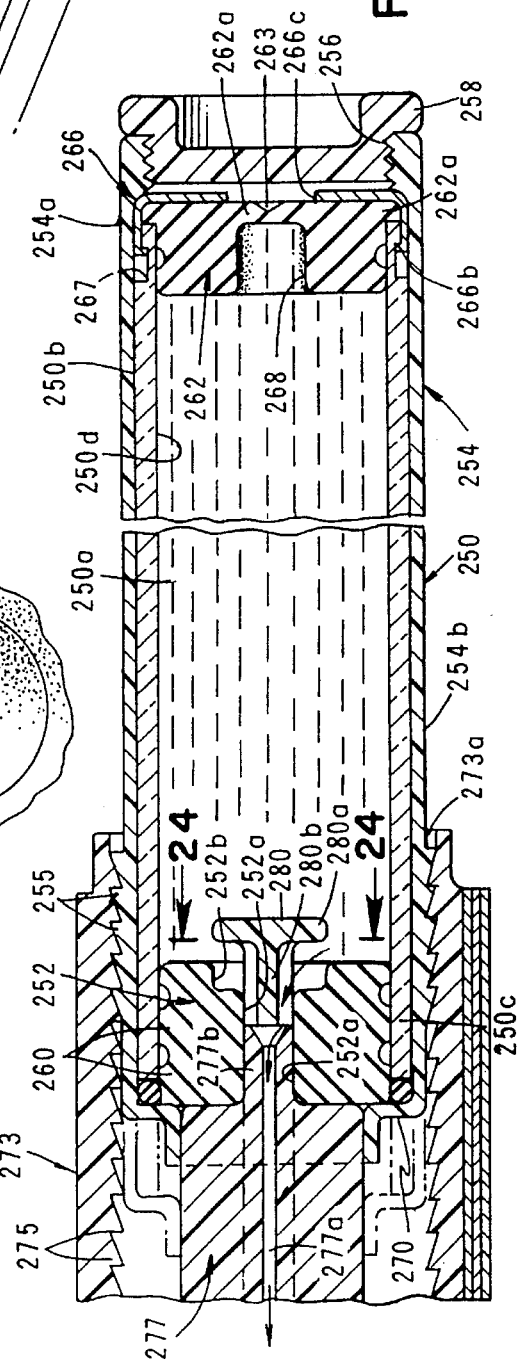
FIG. 22
FIG. 25
FIG. 24
FIG. 23

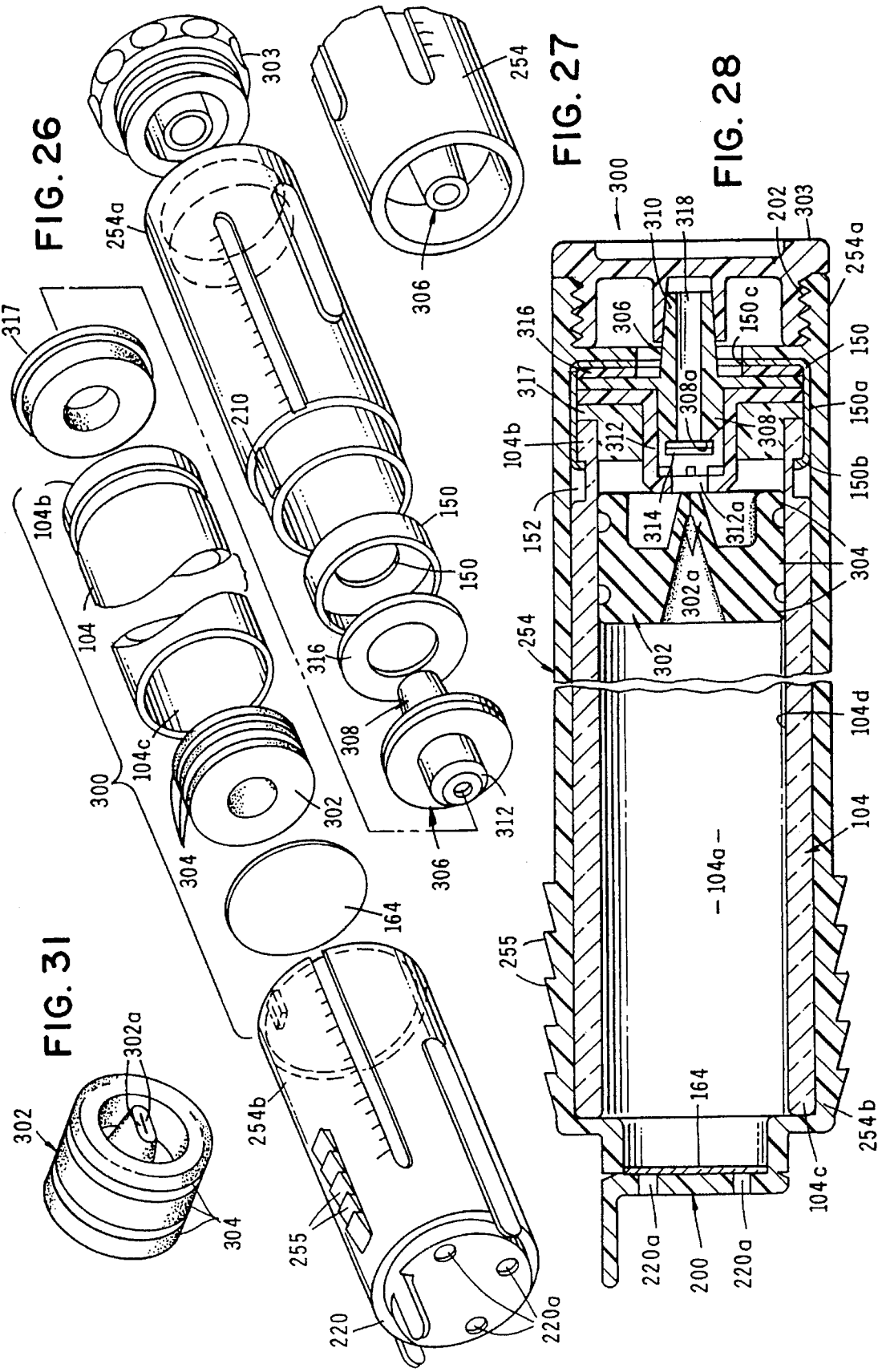

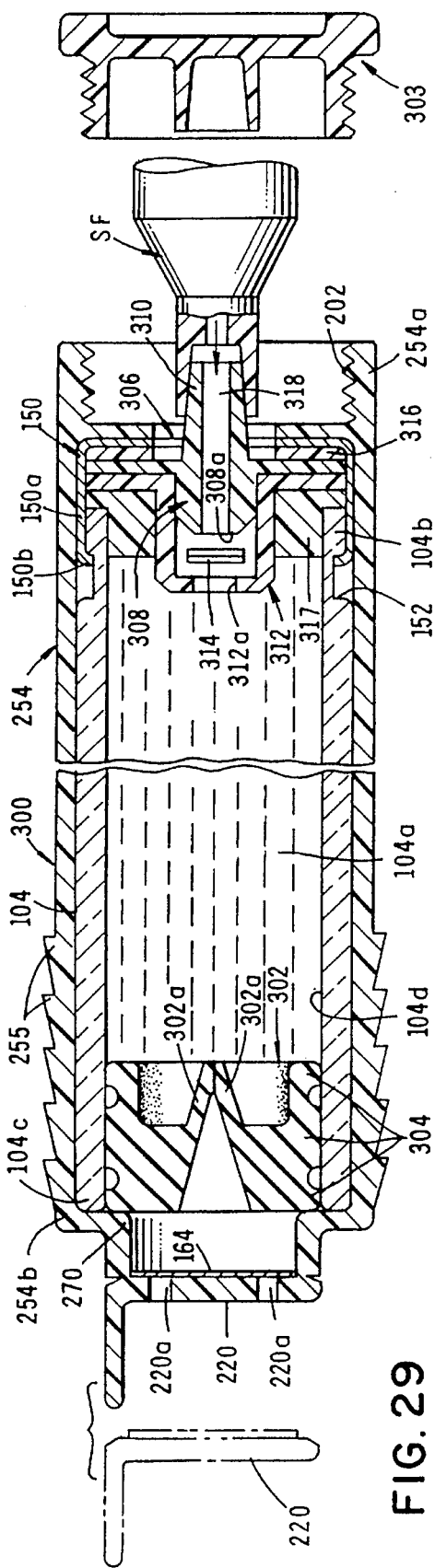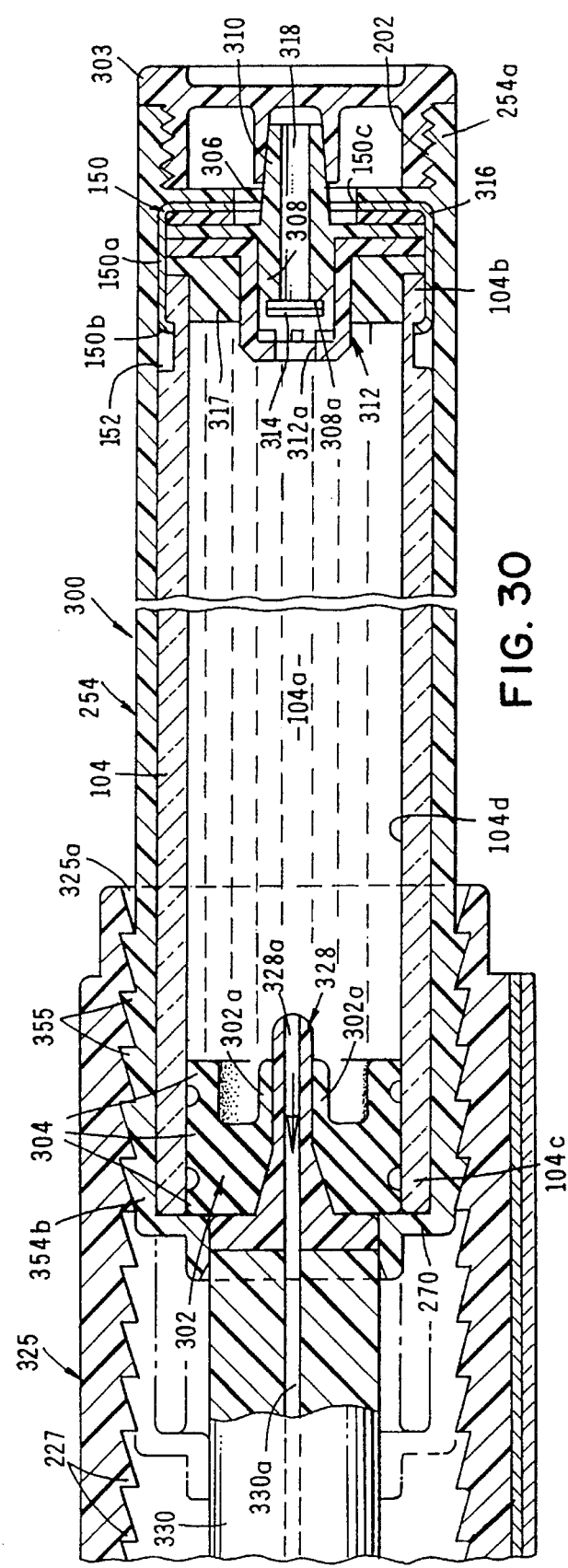

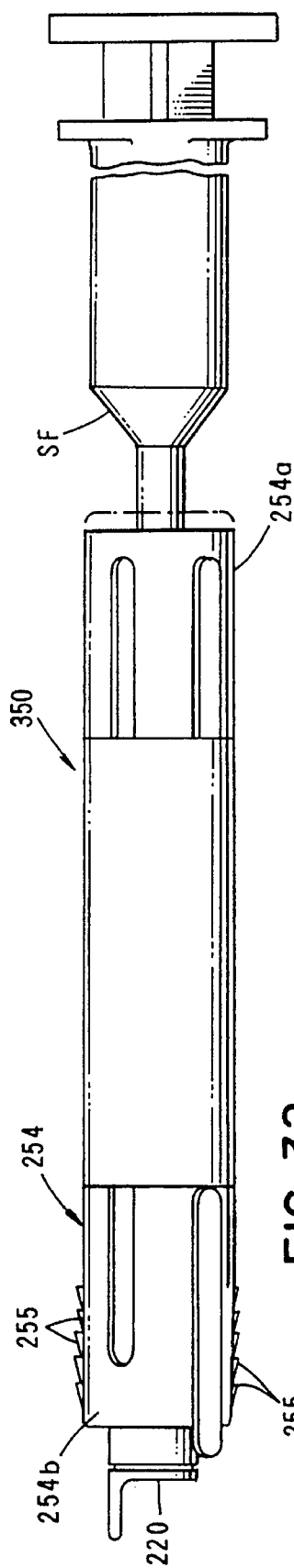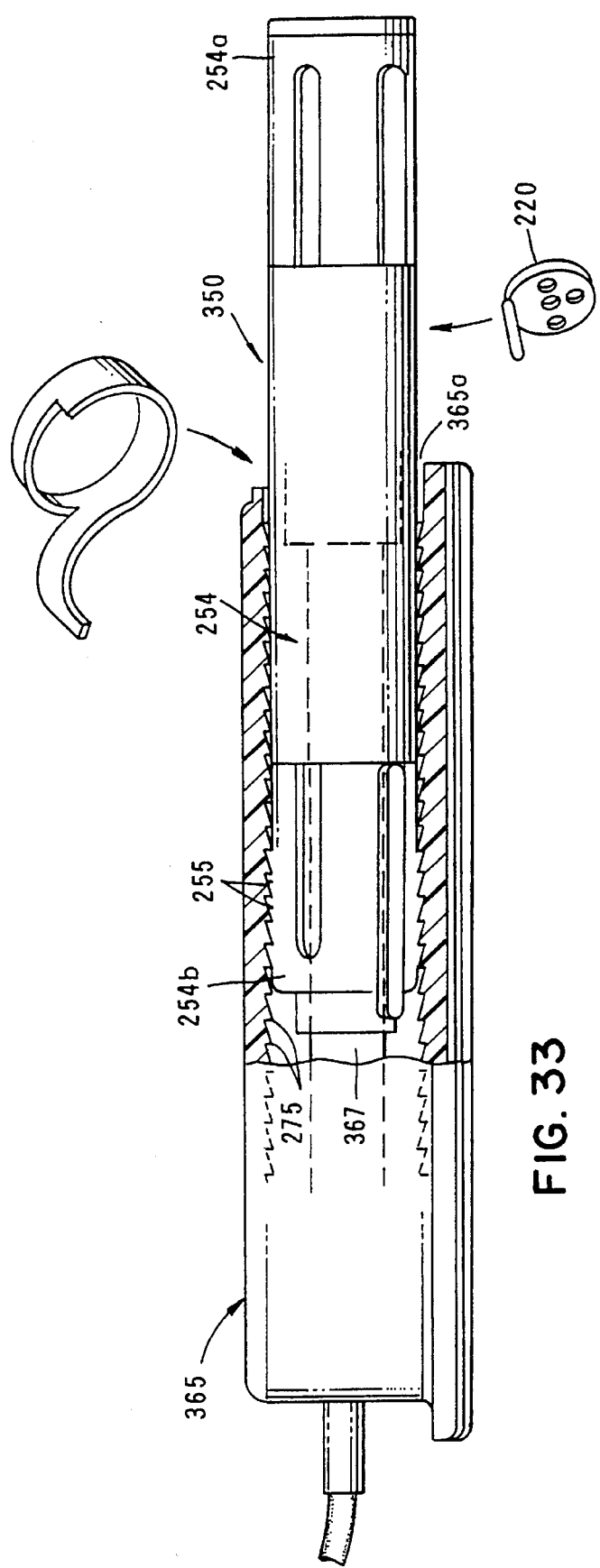
FIG. 32
FIG. 33

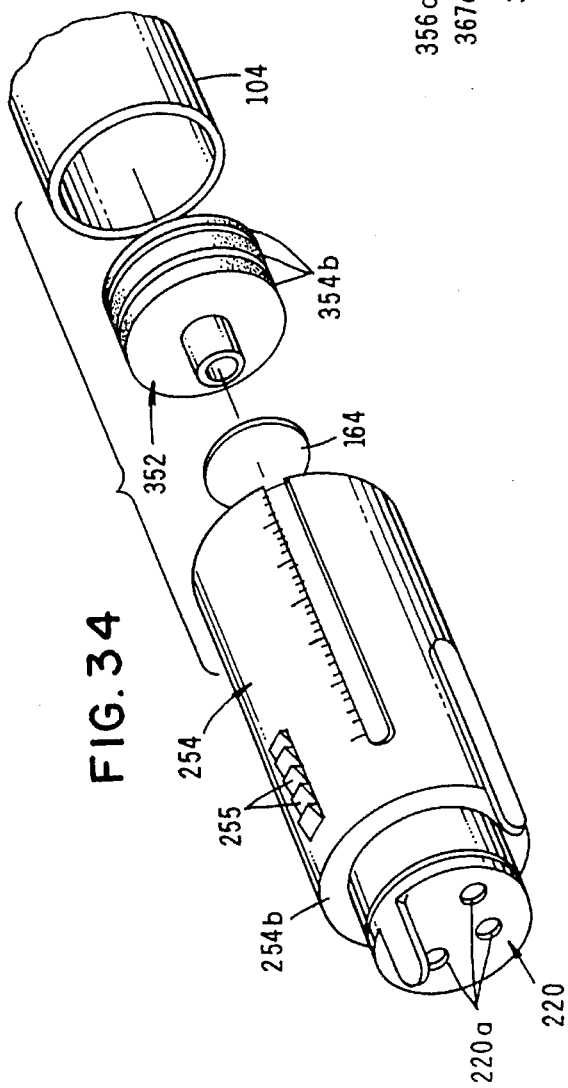
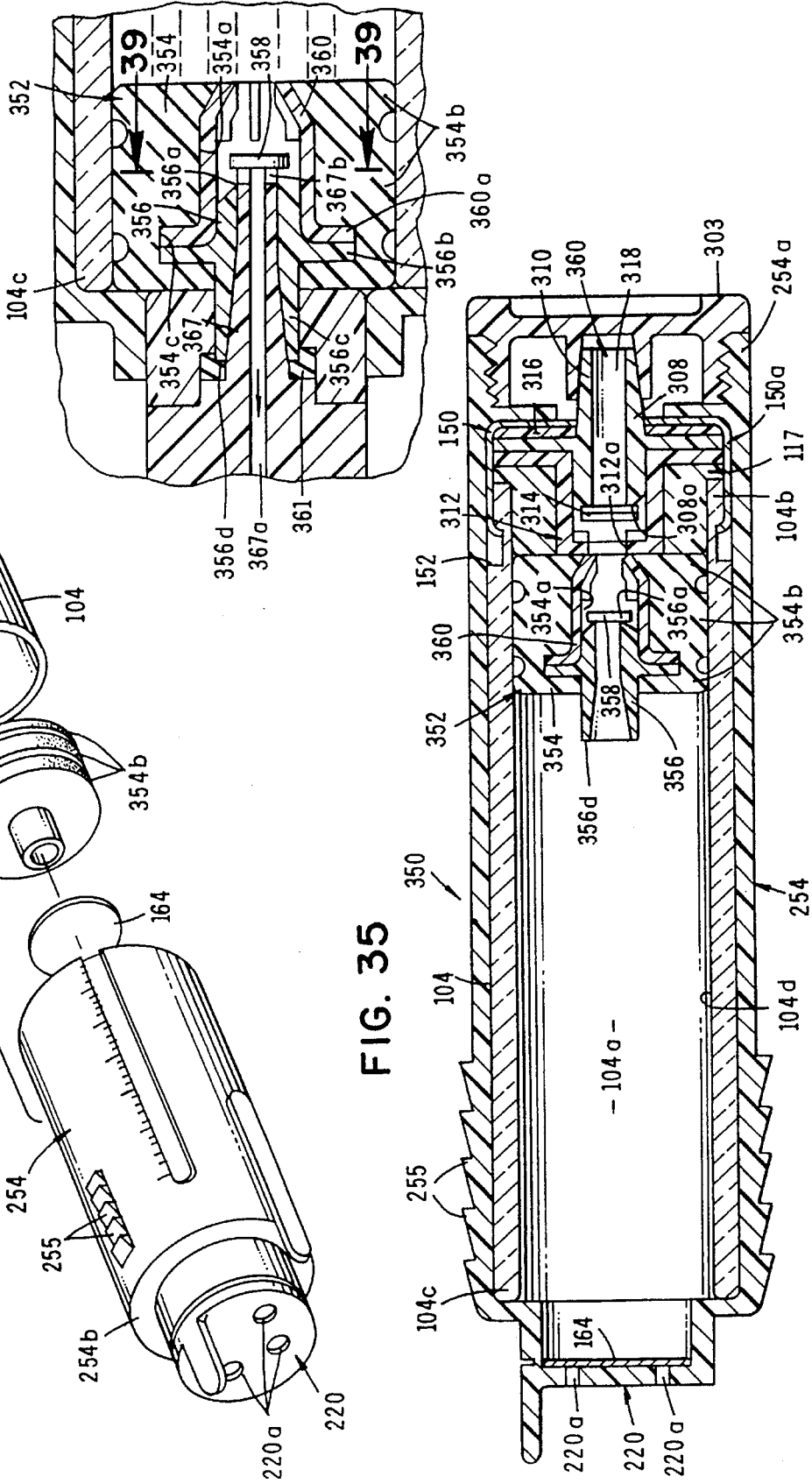

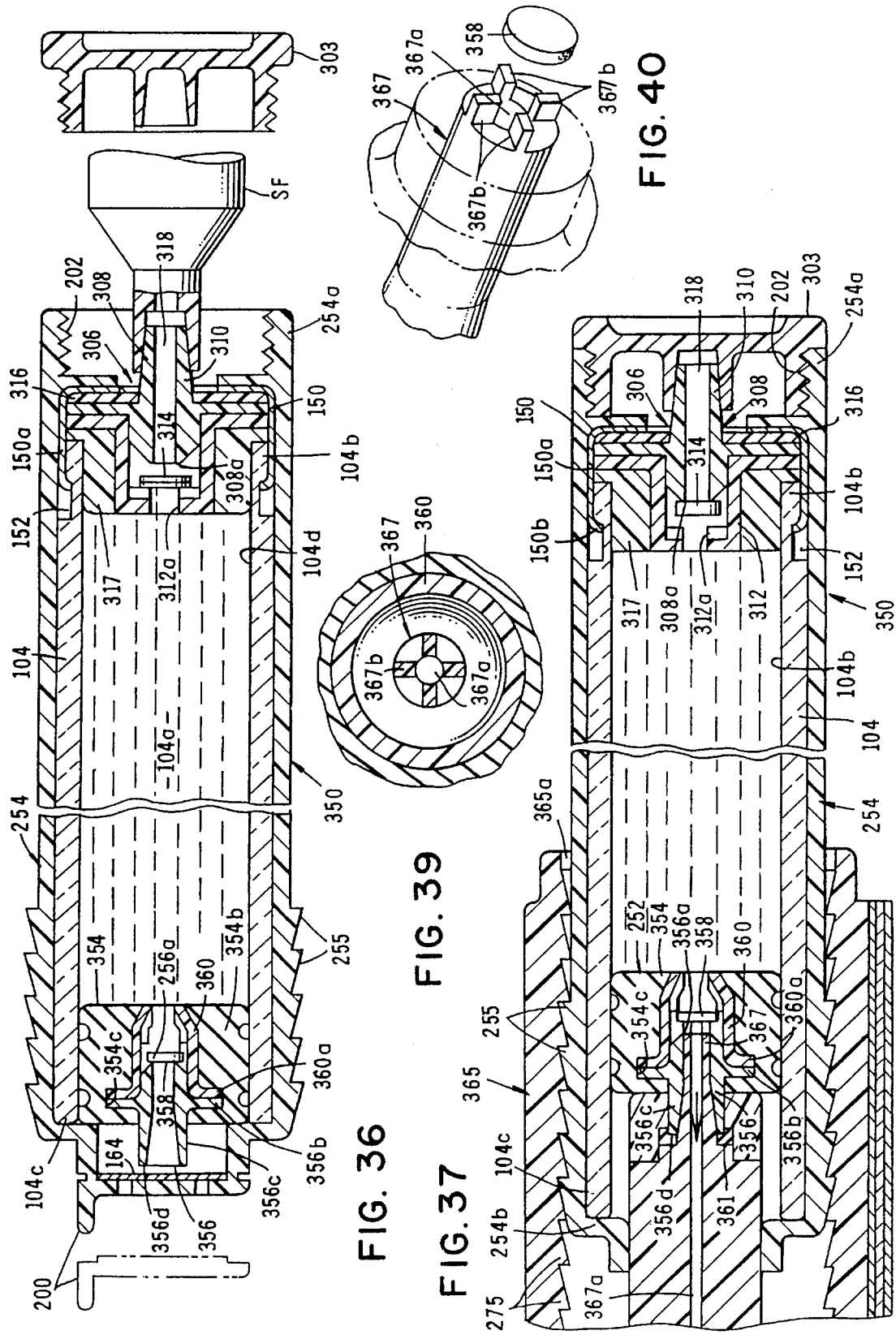

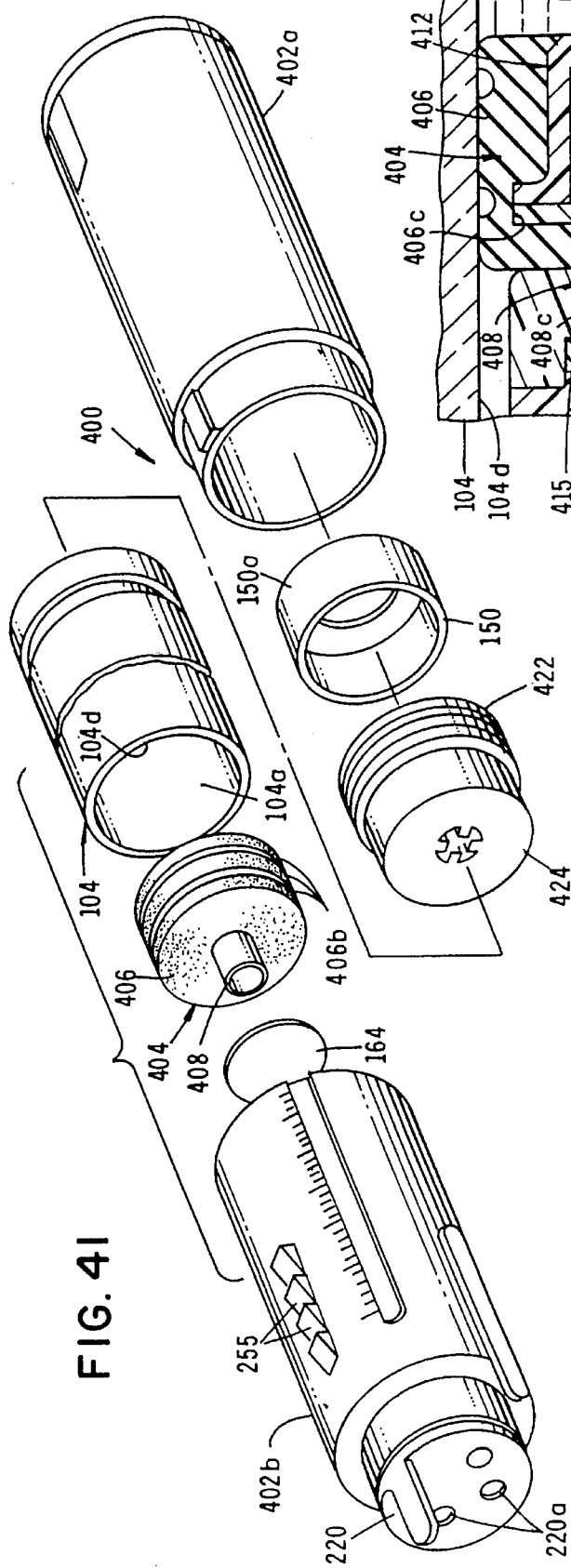
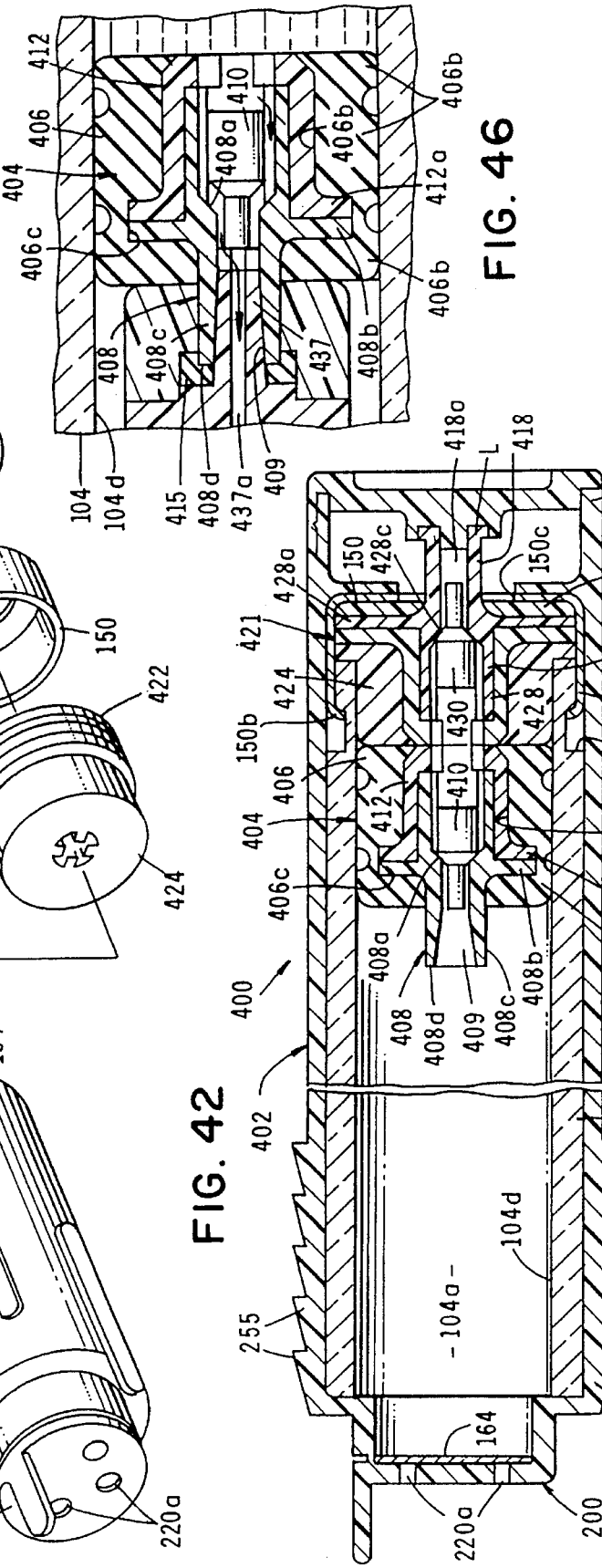
FIG. 41
FIG. 42
FIG. 46

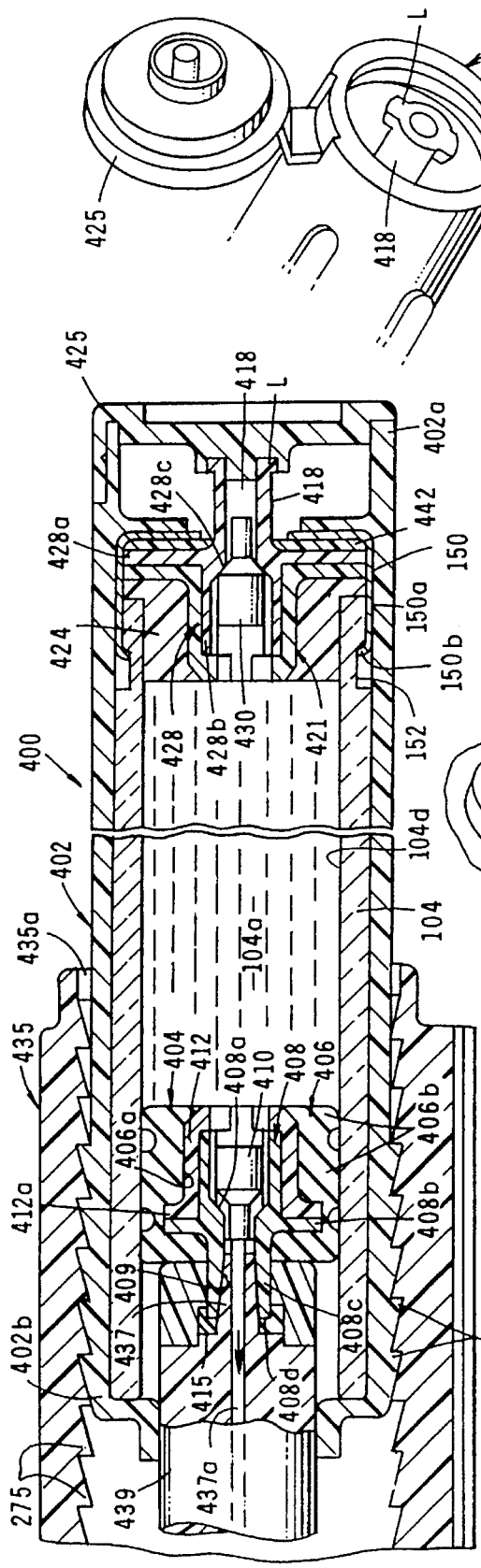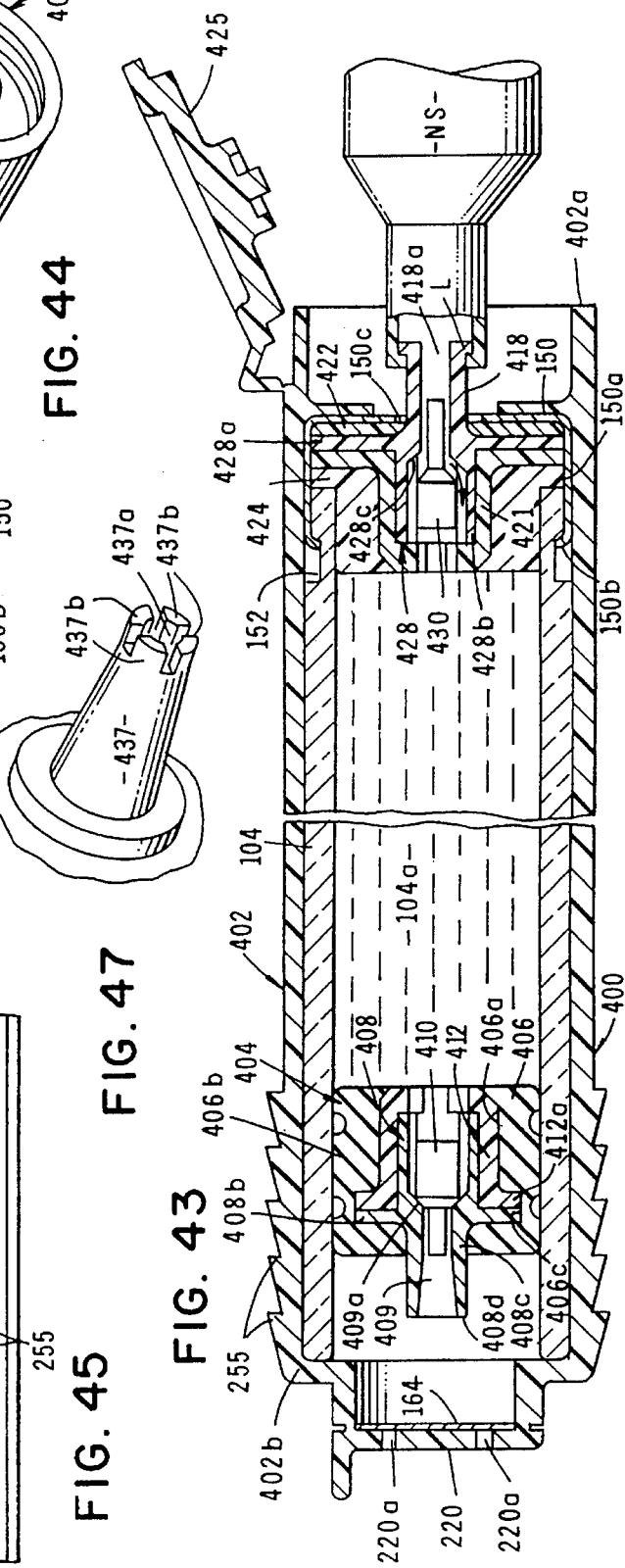

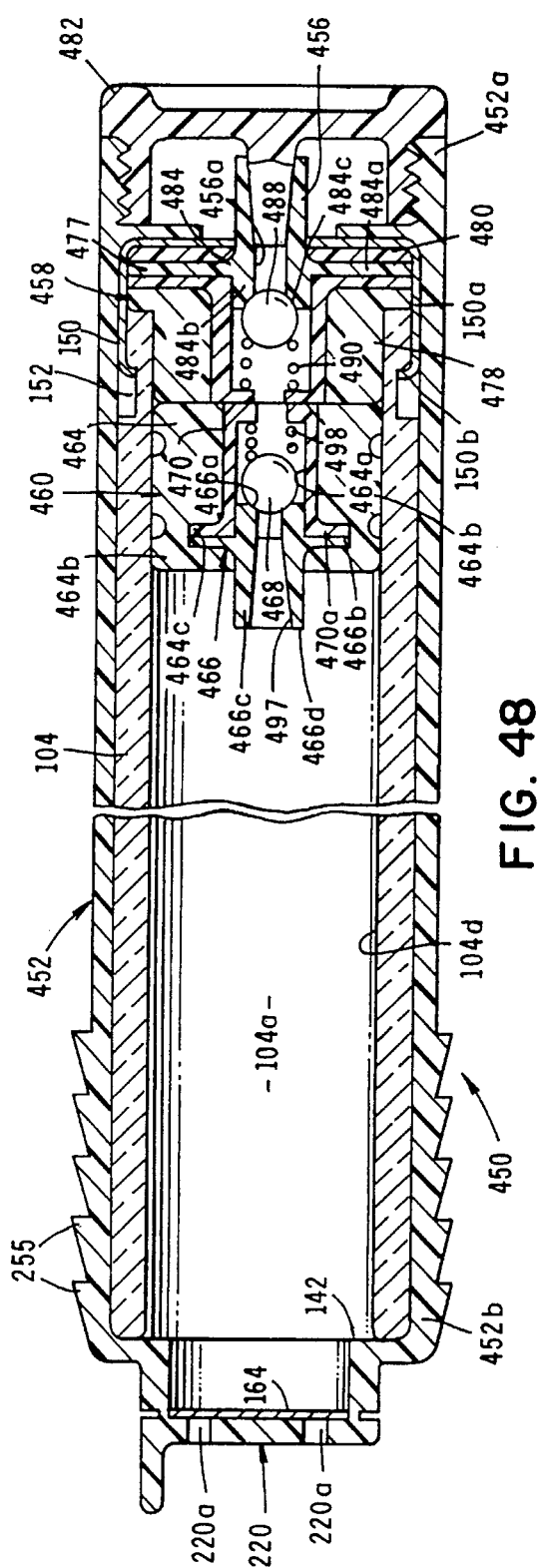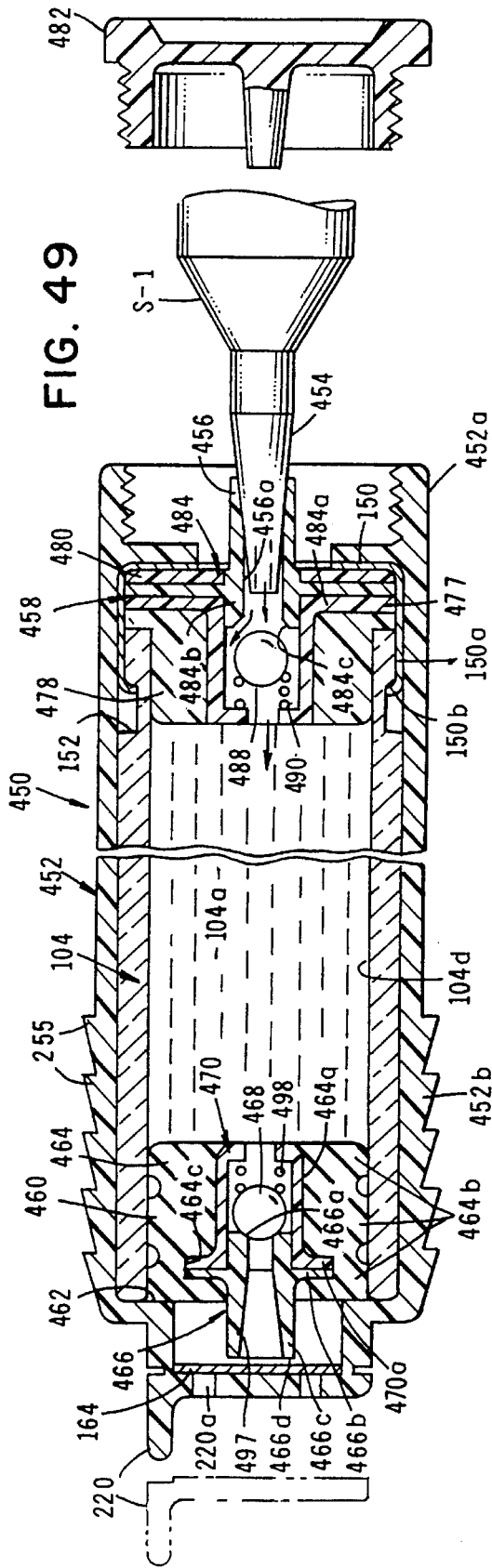
FIG. 48
FIG. 49

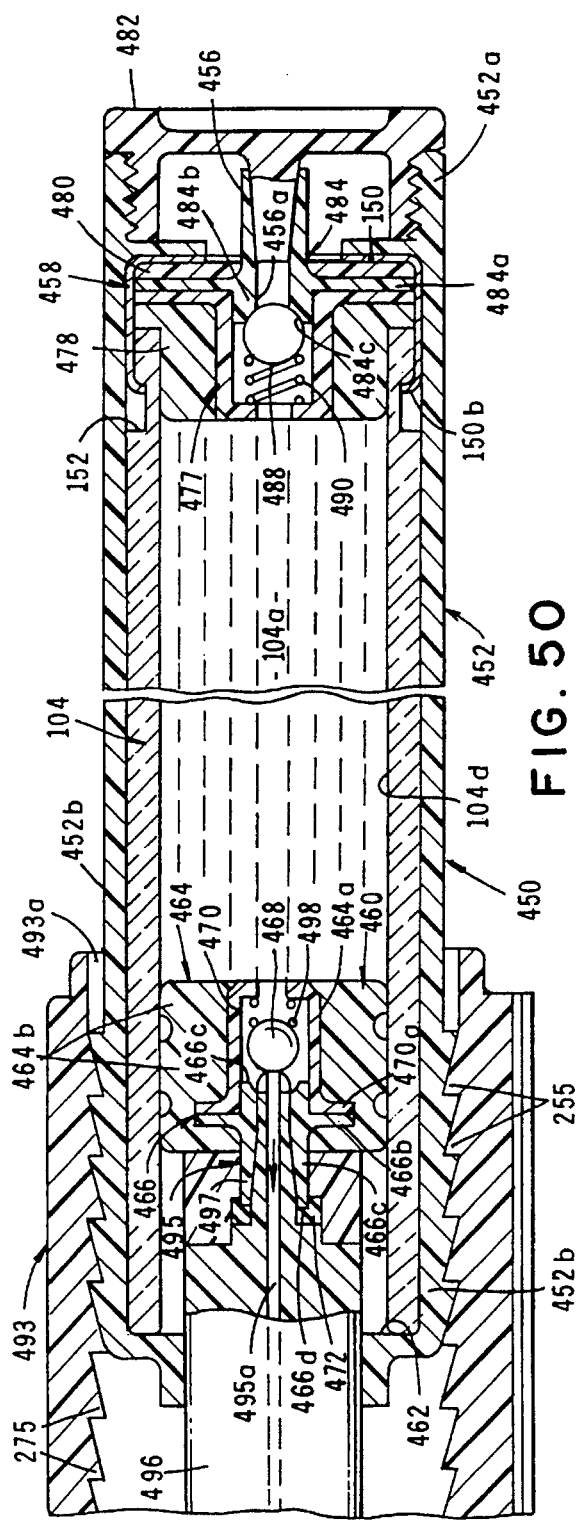
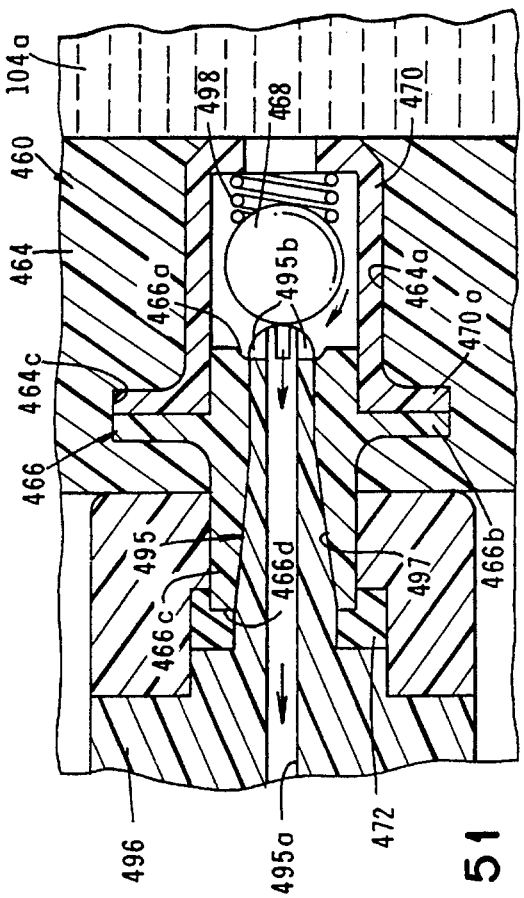
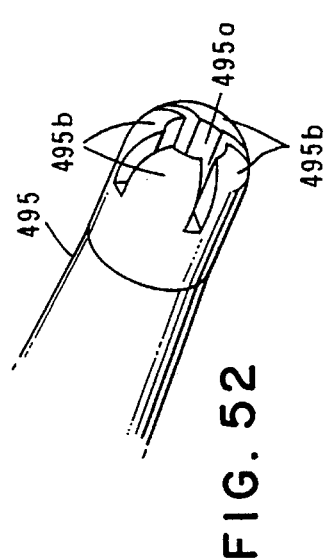
FIG. 50
FIG. 51
FIG. 52

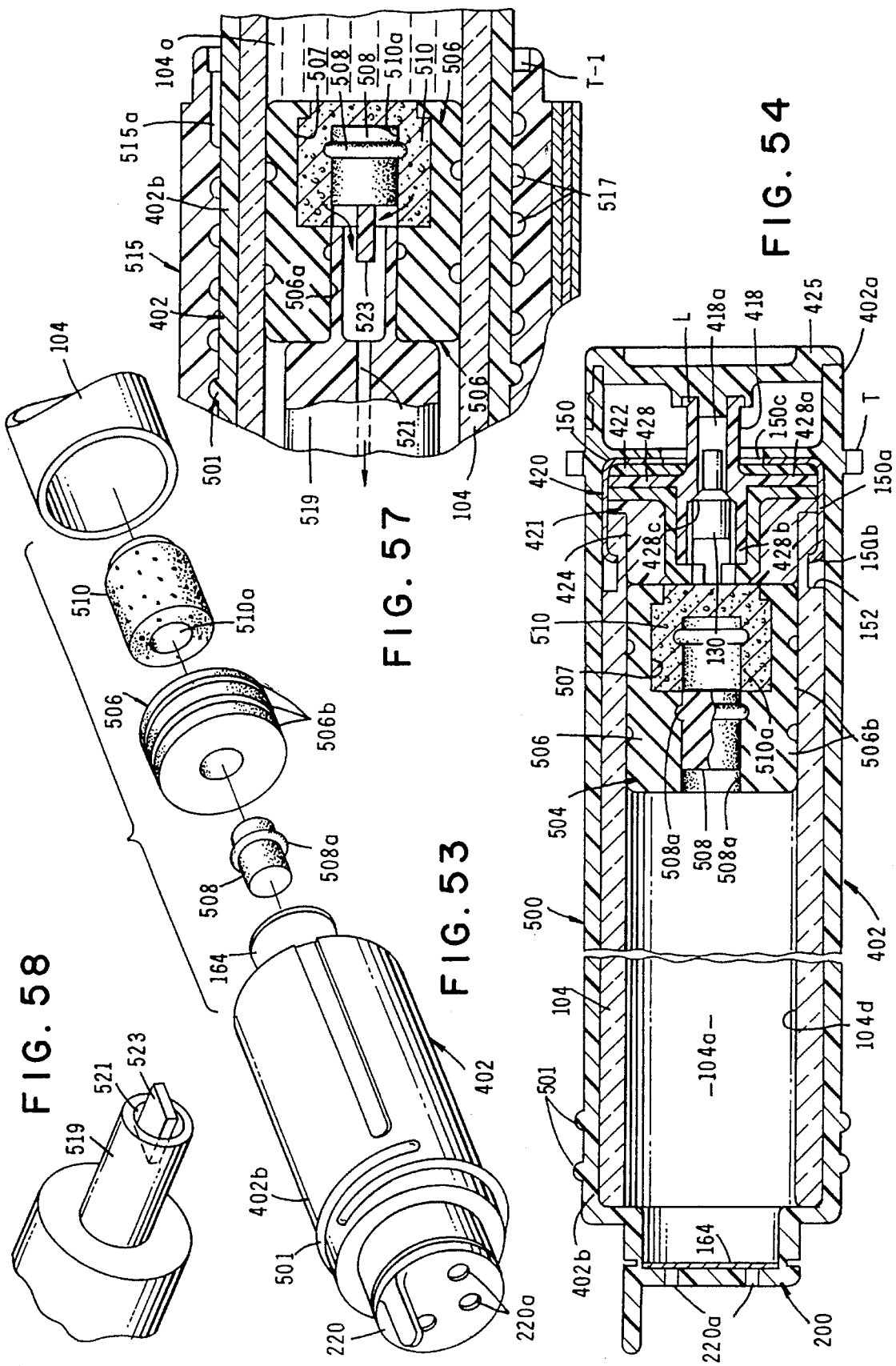

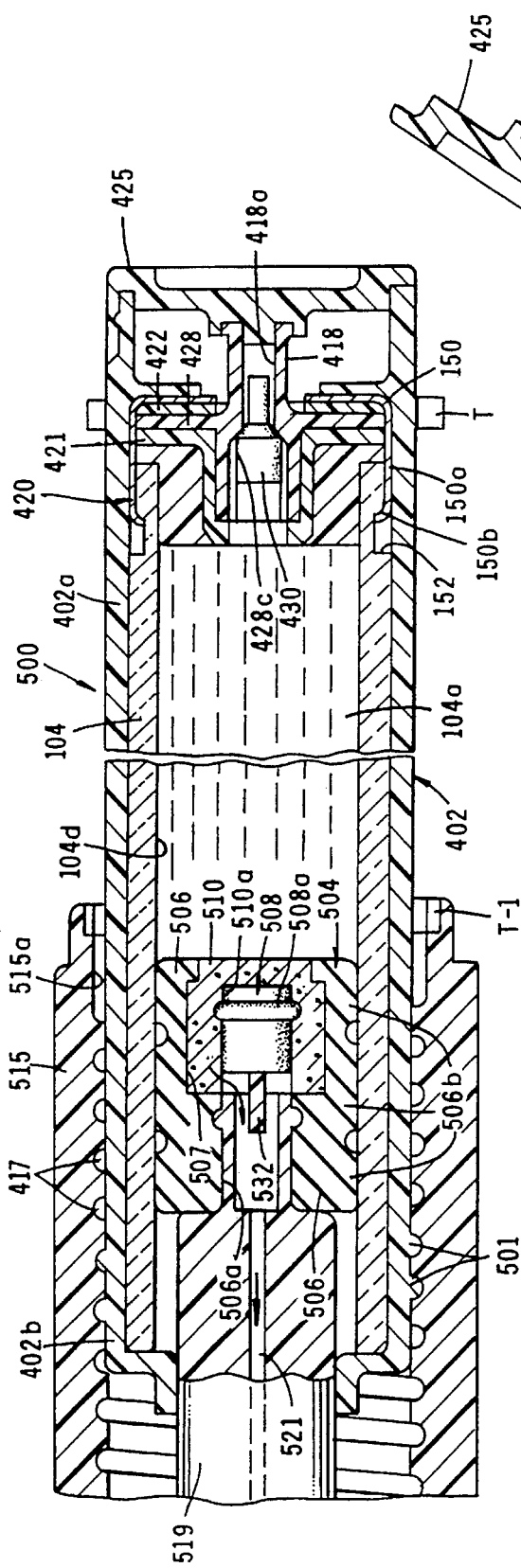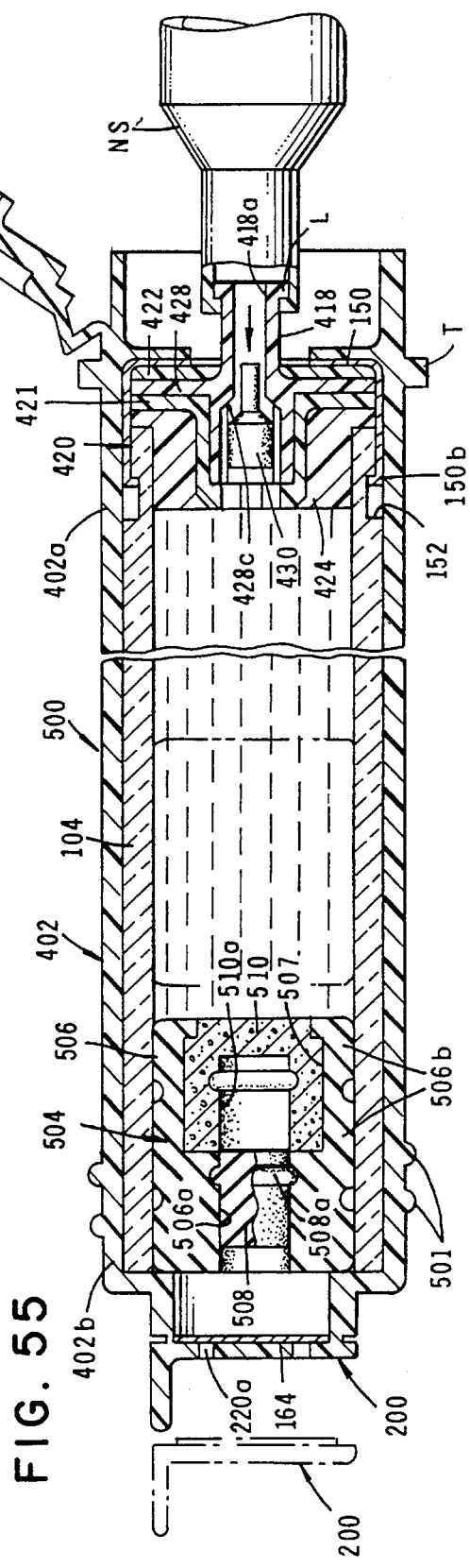

FLUID DELIVERY APPARATUS

This is a continuation in part application of application, filed Sept. 29, 1993, Ser. No. 08/129,470, now U.S. Pat. No. 5,374,256, which is a continuation in part of application, Ser. No. 08/129,693, filed Sept. 29, 1993, now U.S. Pat. No. 5,419,771, which is a continuation in part of Ser. No. 08/069,937 filed May 28, 1993, now U.S. Pat. No. 5,336,188, which is a continuation in part of Ser. No. 08/046,438, filed May 18, 1993, now U.S. Pat. No. 5,411,480, which is a continuation in part of application Ser. No. 07/987,021 filed Dec. 7, 1992 which has now issued into U.S. Pat. No. 5,279,558, which is a continuation of application Ser. No. 07/870,269, filed Apr. 17, 1992, which has now issued into U.S. Pat. No. 5,205,820 and which is, in turn, a continuation in part of application Ser. No. 07/642,208, filed Jan. 16, 1991, which has now issued to U.S. Pat. No. 5,169,389 which is a continuation in part of application Ser. No. 07/367,304 Filed Jun. 16, 1989 which has now issued to U.S. Pat. No. 5,019,047.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time and to a novel fluid containing vial assembly which can be field filled and then used to charge the fluid reservoirs of the fluid delivery apparatus.

2. Discussion of The Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/046,438 filed by the present inventor on Apr. 13, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the devices described in continuation-in-part application, Ser. No. 08/069,937 and illustrated in FIGS. 34 and 35 thereof includes first, second, and third cooperating fluid chambers which can be selectively filled by individual fluid containers or vials containing various fluids such as diluents and medicaments. The novel apparatus shown in FIGS. 34 and 35 permits two or more liquid components to be stored within the reservoirs of the apparatus and then controllably intermixed at the time of fluid delivery. In U.S. application, Ser. No. 08/129,693, there is described a number of inventions which expand on inventions described in the 08/069,937 application by providing a novel platform support system to which several fluid dispensers of varying volume can be operably interconnected. Both this last mentioned application, Ser. No. 08/129,693, as well as Ser. No. 08/069,937 are incorporated herein by reference as though fully set forth herein.

The present application expands further on the concepts disclosed in the applications identified in the preceding paragraph by providing a novel fluid container or vial that is usable with the apparatus of these inventions and is of a unique design which permits it to be expeditiously filled in the field.

SUMMARY OF THE INVENTION

It is an object of the present invention to provide an apparatus for expelling fluids at a precisely controlled rate which is of a compact, low profile, laminate construction. More specifically, it is an object of the invention to provide such an apparatus which can be used for the precise infusion of pharmaceutical fluids to an ambulatory patient at controlled rates over extended periods of time.

It is a particular object of the invention to provide a device of the aforementioned character which embodies stored energy sources such as distendable elastomeric membranes, that form in conjunction with a cooperating base, fluid chambers for containing the fluids to be dispensed. The novel aseptically field fillable vial assembly of the present invention is specially designed for use with these types of devices so that they can be expeditiously filled in the field shortly before use with a wide variety of medicinal fluids.

By way of summary description, the novel vial construction of the present invention permits field filling of either individual fluid dispensers of the character described in the preceding paragraphs, or alternatively, permits the field filling of multireservoir devices which allow for the controlled delivery therefrom of large volumes of the same or different fluids at controlled rates in accordance with a predetermined delivery protocol.

In one form of the fluid container of the present invention, the fluid chamber thereof can also be quickly and easily filled in the field using a conventional hypodermic syringe. After filling, the vial assembly can be coupled with the delivery system in a manner to insure the aseptic transfer of the fluid to be delivered.

Another object of the invention is to provide field fillable vial assemblies of the class described which can be filled and then stored under refrigeration for an extended period. For those types of assemblies, a novel temperature indicator is provided as an integral part of the assembly.

Another object of the invention is to provide field fillable vial assemblies which can be expeditiously filled by automated filing machines located either in the hospital pharmacy or by the home health-care pharmacist.

Other objects of the invention are set forth in U.S. Pat. No. 5,205,820 and Ser. No. 08/069,937 which are incorporated herein and will become more apparent from the discussion which follows.

BRIEF DESCRIPTION OF THE DRAWINGS

FIG. 1 is a generally perspective, exploded view of one form of the field filled vial assembly of the present invention showing it being filled by means of a conventional hypodermic syringe.

FIG. 2 is an exploded, generally perspective view of one form of the fluid container or vial assembly of the invention.

FIG. 5 is a generally perspective, exploded view of an alternate form of the field filled vial assembly of the present invention.

FIG. 5A is a fragmentary, generally perspective view of a check valve assembly of the assembly shown in FIG. 5.

FIG. 6 is a fragmentary, generally perspective view of the fill end portion of the assembly shown in FIG. 5.

FIG. 7 is a generally perspective illustrating view showing the assembly of FIG. 5 being filled by a conventional syringe having a luer type connector.

FIG. 8 is an enlarged, foreshortened, cross-sectional side view of the vial assembly of FIG. 5.

FIG. 8A is an enlarged cross-sectional view taken along lines 8A—8A of FIG. 8.

FIG. 9 is a fragmentary, cross-sectional, exploded view of the fill end portion of the assembly showing the removal of the end cap and the interconnection of a syringe with the fill end portion.

FIG. 10A is a fragmentary, generally perspective view of a check valve assembly of the assembly shown in FIG. 10.

FIG. 20 is a generally perspective, exploded view of another form of the field filled vial assembly of the present invention adjusted to be filled by means of a blunt cannula.

FIG. 21 is an enlarged, cross-sectional side view of the vial assembly shown in FIG. 20.

FIG. 22 is an enlarged cross-sectional view of the device of the invention shown in FIG. 21 with the cap having been removed and the fluid chamber being filled with a syringe provided with a blunt cannula.

FIG. 23 is a cross-sectional view similar to FIG. 22 but showing the vial assembly mated with a fluid dispenser having a valve operating member for opening the fluid outlet valve of this last form of the invention.

FIG. 24 is a cross-sectional view taken along lines 24—24 of FIG. 23.

FIG. 25 is a fragmentary, generally perspective view of the fluid outlet valve of the vial assembly and the valve operating means of the fluid dispenser.

FIG. 26 is a generally perspective, exploded view of still another form of the field filled vial assembly of the present invention which is adapted to be filled by means of a slip-fit luer connector.

FIG. 27 is a fragmentary, generally perspective view of the fill end portion of the vial assembly shown in FIG. 26.

FIG. 28 is an enlarged, cross-sectional side view of the vial assembly shown in FIG. 26.

FIG. 29 is an enlarged, cross-sectional view of the device of the invention shown in FIG. 28 with the cap having been removed and the fluid chamber having been filled with a syringe provided with a slip-fit luer connector.

FIG. 30 is a cross-sectional view similar to FIG. 29, but showing the vial assembly mated with a fluid dispenser having means for opening the duck-bill type fluid outlet valve of this last form of the invention.

FIG. 31 is a generally perspective view of the duckbill type fluid outlet valve.

FIG. 32 is a side elevational view of another form of vial assembly specially designed for use with cardet type dispensers of the character described in U.S. Ser. No. 08/129, 693 and generally shown in FIG. 23 of the application.

FIG. 33 is a side elevational view, which is partly broken away to shown internal construction, showing the vial assembly mated with a typical cardet type dispenser unit.

FIG. 34 is a fragmentary, generally perspective, exploded view of the fluid outlet portion of the vial assembly shown in FIG. 32.

FIG. 35 is an enlarged, cross-sectional side view of the vial assembly shown in FIG. 32.

FIG. 36 is an enlarged cross-sectional view of the device of the invention shown in FIG. 35 with the cap having been removed and the fluid chamber having been filled with a syringe provided with a slip-fit luer connector.

FIG. 37 is a cross-sectional view similar to FIG. 36, but showing the vial assembly mated with a fluid dispenser of the character usable with cardet type platform supports.

FIG. 38 is an enlarged, cross-sectional view of part of the left portion of FIG. 37, showing greater detail of construction.

FIG. 39 is a cross-sectional view taken along lines 39—39 of FIG. 38.

FIG. 40 is an enlarged, generally perspective view of the fluid outlet valve operating member of the fluid dispenser of FIG. 37.

FIG. 41 is a generally perspective, exploded view of yet another form of the field filled vial assembly of the present invention which is adapted to be filled by means of a syringe provided with a conventional luer connector.

FIG. 42 is an enlarged, cross-sectional side view of the vial assembly shown in FIG. 41.

FIG. 43 is an enlarged, cross-sectional view of the device of the invention shown in FIG. 42 with the cap having been removed and the fluid chamber being filled with a syringe provided with a conventional luer connector.

FIG. 44 is a generally perspective view of the fill end portion of the vial assembly shown in FIG. 43.

FIG. 45 is a cross-sectional view similar to FIG. 43 but showing the vial assembly mated with a fluid dispenser also having an outlet valve operating member.

FIG. 46 is an enlarged, cross-sectional view of part of the left portion of FIG. 45 showing greater detail of construction.

FIG. 47 is a generally perspective fragmentary view of the fluid outlet valve operating member of the fluid dispenser.

FIG. 48 is a cross-sectional side view of another form of vial assembly of the present invention.

FIG. 49 is an enlarged, cross-sectional view of the device of the invention shown in FIG. 48 with the cap having been removed and the fluid chamber having been filled with a syringe provided with a slip-fit connector.

FIG. 50 is a cross-sectional view similar to FIG. 49 but showing the vial assembly mated with a fluid dispenser also having a fluid outlet valve operating member of unique construction.

FIG. 51 is an enlarged, cross-sectional view of part of the left portion of FIG. 50 showing additional detail of construction.

FIG. 52 is a generally perspective fragmentary view of the fluid outlet valve operating member.

FIG. 53 is a generally perspective, exploded view of still another form of the field filled vial assembly of the present invention which is adapted to be filled by means of a conventional luer type syringe.

FIG. 54 is an enlarged, cross-sectional side view of the vial assembly shown in FIG. 53.

FIG. 55 is an enlarged, cross-sectional view of the device of the invention shown in FIG. 54 with the cap having been removed and the fluid chamber having been filled with the syringe.

FIG. 56 is a cross-sectional view similar to FIG. 55 but showing the vial assembly mated with a fluid dispenser having a valve operating member.

FIG. 57 is an enlarged, cross-sectional view of a part of the left portion of FIG. 56 showing additional detail of construction.

FIG. 58 is a generally perspective fragmentary view of the fluid outlet valve operating member of the dispenser of this latest form of the invention.

DESCRIPTION OF THE INVENTION

Figure 3:
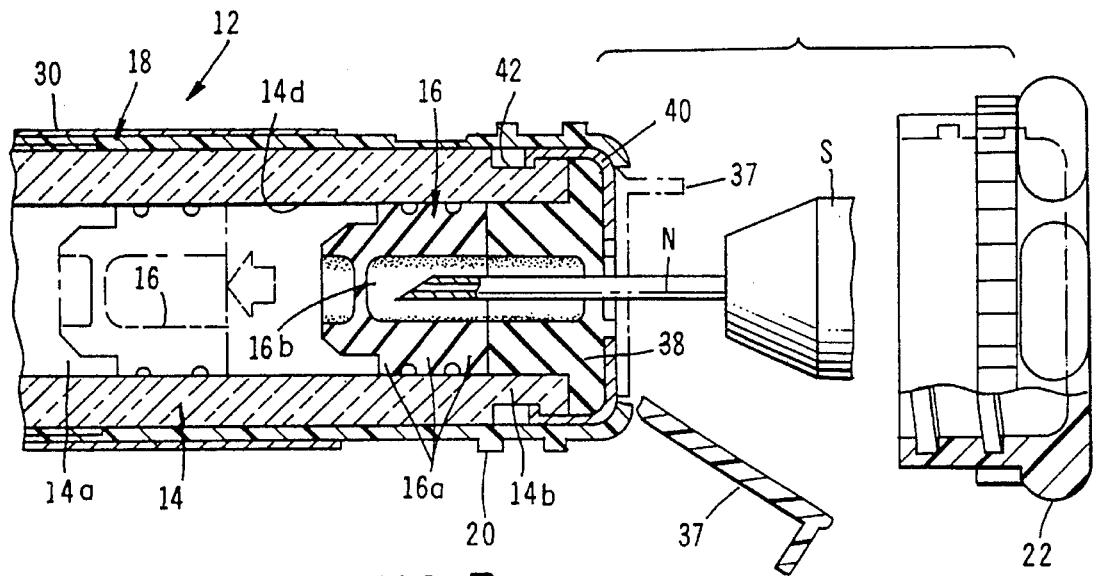
FIG. 3 is an enlarged, fragmentary, cross-sectional side view of the vial assembly showing the cap removed and the internal plunger thereof being pierced by the syringe needle.

Referring to the drawings and particularly to FIGS. 1 through 3, one form of the vial assembly of the invention is there illustrated and generally identified by the numeral 12. The apparatus comprises a transparent container, or vial, 14 having a fluid chamber 14a for containing the fluid to be added to the reservoir of a fluid dispenser or other fluid delivery device. The fluid can be a diluent or any of the medicaments or beneficial agents described in the previously identified U.S. Pat. No. 5,205,820. Vial 14 has open ends 14b and 14c and closely receives a pierceable piston-like plunger 16 which is movable within vial 14 from a first position, shown in FIG. 3, where it is proximate end 14b of the vial to a second position where it is disposed proximate end 14c of the vial. Container 14 can be a glass vial or any other suitable sterile container for containing the fluid that is to be used in filling the reservoirs of the fluid dispensers or fluid delivery devices.

Also forming a part of the vial assembly of the present embodiment of the invention is an outer safety casing 18, shown here as comprising cooperating first and second portions 18a and 18b which are joined to form a sterile barrier system. First portion 18a is provided with threads 20 and is closed by a threaded closure cap 22. Provided at its open end is a socket like construction 24 which is telescopically received within the open end portion 26 of second casing portion 18b. Outer casing 18 is receivable over vial 14 and portions 18a and 18b are held in mating engagement by an overwrap 30 which functions as an interface sterility barrier and upon which appropriate identifying indicia 32 can be imprinted. A novel temperature indicator means, such as indicator "T" is also carried by overwrap 30 indicator "T" may be a reversible liquid crystal temperature bar indicator of a character which is readily commercially available from sources such as Clark Research and Development of Chicago, Ill., Thermax of Anaheim, Calif. and American Thermo Instruments of Dayton, Ohio. Indicator "T" provides information as to the approximate temperature of the vial assembly during storage and at time of use.

As shown in FIG. 2, a guide bead 32 is provided on portion 24. Bead 32 is receivable within a corresponding channel 33 provided in portion 18b to insure that portions 18a and 18b of the outer casing are properly aligned.

In a manner presently to be described, as the fluid chamber of the vial is filled with fluid using syringe "S" (FIG. 1), penetrable piston 16 is moved within the vial from the first position shown in FIG. 3 to a second position wherein it is disposed proximate end 14c. Piston 16 is provided with a plurality of circumferentially extending sealing beads 16a which sealably engage the inner walls 14d of container 14 as the piston moves rearwardly thereof so as to prevent fluid leakage past the piston.

Referring now to FIG. 3, after the vial assembly has been assembled in the manner shown in FIG. 1 and with cap 22 removed, a tear away closure cover 37 is removed. Next the needle "N" of the syringe "S" is used to penetrate a pierceable means shown here as an elastomeric plug 38 which closes end 14b of vial 14. As shown in FIG. 3, plug 38 is held in position within vial 14 by an aluminum crimp cap 40, the periphery of which is crimped over into a circumferential groove 42 provided proximate end 14b of the vial. As fluid is forced from the syringe into an interior chamber 16b of plunger 16, the plunger will be forced to the left until it moves into close proximity with end 14c of the vial where it engages a retainer ring 44 (FIG. 2) that is closely received within end 14c of the vial. During the vial filling step, air disposed within chamber 14a will be expelled through a sterile vent patch 45 which is bonded to a closure cap 46 that is provided with vent apertures 46a.

After the vial has been filled with the selected fluid, cap 22 is reconnected with the outer casing 18 so as to maintain the interior of the vial in a sealed, aseptic condition. As best seen in FIG. 2, casing 18 is provided with an elongated viewing slot 50 that permits viewing of the interior chamber 14a of the vial. Similarly, overwrap 30 has an elongated viewing slot 52 which is indexable with slot 50. With this construction, the user can tell at a glance whether the vial is full or empty.

In its sealed, aseptic condition with a sterile fluid path, vial assembly 12 can be stored as may be necessary until it is to be used to fill a fluid dispenser or a reservoir of a delivery apparatus such as that shown in FIGS. 34 and 35 of U.S. Ser. No. 08/069,937.

Figure 4:
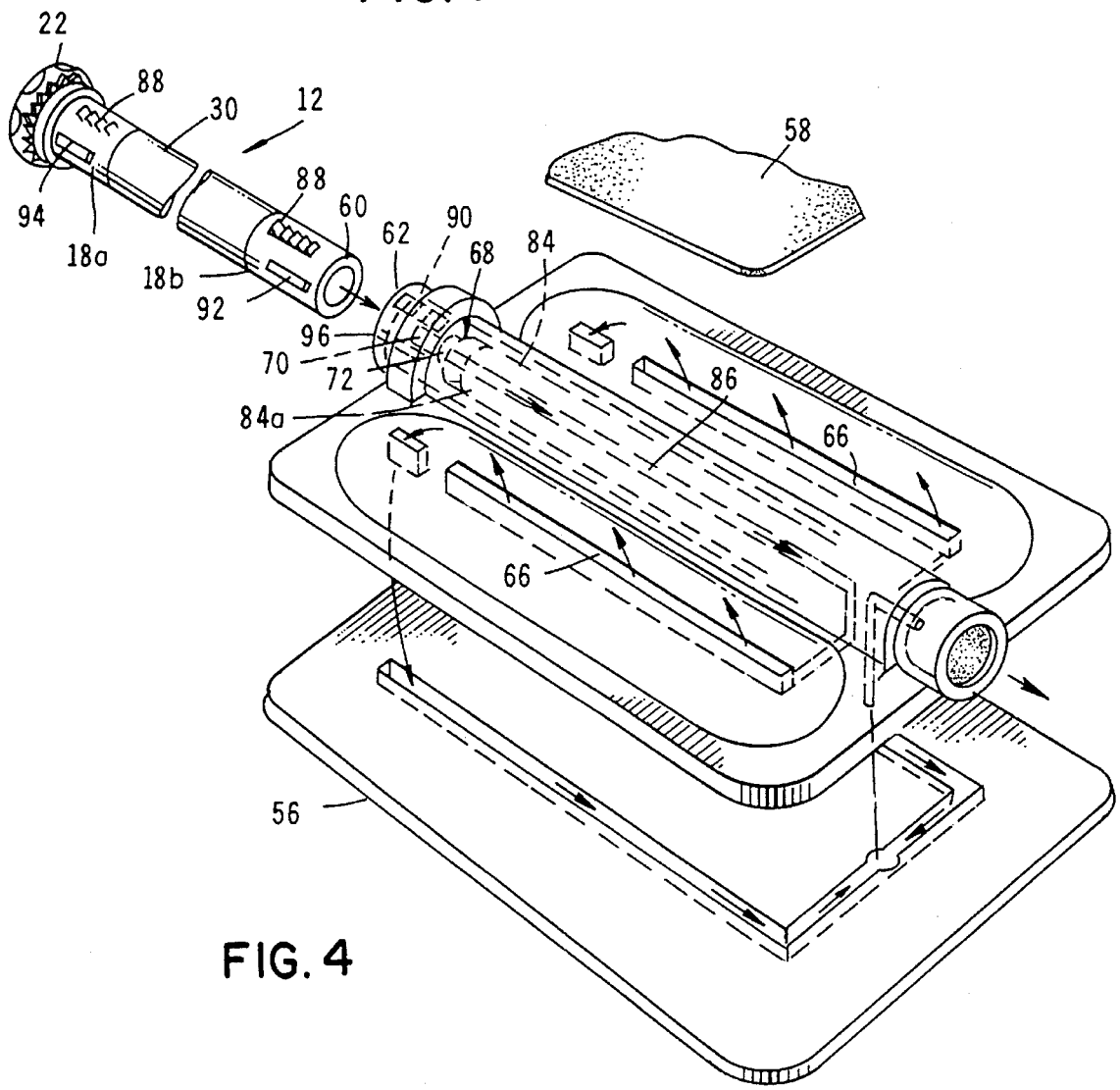
FIG. 4 is a fragmentary, perspective view of one form of the fluid dispenser with which the vial assembly of the present invention can be used.

Turning now to FIG. 4, the vial assembly is there shown being used to fill the fluid chamber of a fluid dispenser of the character having a base 56, a stored energy means for forming, in conjunction with the base, a fluid chamber and a cover means which is receivable over the base for sealably enclosing the stored energy means. The stored energy means is here shown as comprising a distendable membrane 58, of the general character described in U.S. Pat. No. 5,205,820 at Column 9, Lines 3–59. The cover means (not shown) comprises a cover 34 of the general character shown in FIG. 61 of U.S. Pat. No. 5,205,820. Reference should be had to these patents for a full understanding of the construction and operation of the fluid dispenser shown in FIG. 4.

After tear-away cover 46 has been removed from the vial assembly (FIG. 2), the outboard end 60 of the vial assembly, which presents a sterile interface, is inserted into the likewise sterile inlet opening 62 of the dispenser unit to accomplish a sterile coupling. As indicated in FIG. 4, the dispenser unit is provided with first flow means for establishing sterile fluid communication between the fluid inlet 66 of the reservoirs of the fluid dispenser and chamber 14a of vial 14, when the filling assemblage is mated with the fluid dispenser. In the embodiment of the invention, shown in FIG. 4, the first flow means comprises a piercing cannula assembly 68 which includes an outwardly protruding hollow cannula 70. The cannula assembly 68 also includes a housing 72 which supports hollow needle 70. Housing 72 is connected to the outboard end 84a of an elongated stem 84 which is provided with a central fluid passageway 86 that communicates with the reservoirs of the fluid dispenser.

After end 60 of the vial assembly is inserted into inlet port 62 of the fluid dispenser, an inward pressure exerted against the vial assembly will cause hollow cannula 70 to penetrate penetrable elastic septal plug 38 piston 16 of the vial assembly opening a fluid flow passageway between passageway 86 of the fluid dispenser and chamber 14a of the vial assembly. As shown in FIG. 4, casing 18b of the vial subassembly is provided with a multiplicity of outwardly extending, resiliently deformable locking elements 88, which comprise a part of the interlocking means of the invention for interlocking together the vial assembly and the fluid dispenser. Elements 88 are adapted to slide past a multiplicity of inwardly extending teeth 90 provided within inlet 62 of the fluid dispenser. These teeth are so constructed and arranged as to engage elements 88 in a manner to permit insertion of the vial assembly into the dispenser inlet but to prevent its removal after it has been fully telescopically inserted into the inlet of the fluid dispenser. To insure proper alignment between the filling subassembly and the inlet of the fluid dispenser, forward and rearward guide rails 92 and 94 are closely receivable within longitudinally extending tracks 96 provided within the inlet of the fluid dispenser.

As previously mentioned, indicator means are provided for indicating the volume of fluid remaining within vial 14 as the vial assembly is inserted into the inlet of the fluid dispenser. This indicator means comprises the previously identified viewing slots 50 and 52 along which are disposed a multiplicity of indicating indicia 97 (FIG. 2). Since vial 14 is transparent, the amount of fluid remaining within the vial at any point in time can readily be determined by merely aligning one of the indicia markings on the casing with the inboard extremity of piston 16 as it moves toward its innermost position.

As previously mentioned, the vial assemblies of the present invention can also be conveniently coupled with connector means 414a, 414b and 414c of the multireservoir devices illustrated in FIGS. 34 and 35 of U.S. Ser. No. 08/069,937 and can be used to fill the reservoirs of these devices in the manner described in this co-pending application. As a study of this earlier application will make clear, the manner of coupling of the vial assemblies herein described with the devices disclosed in U.S. Ser. No. 08/069,937.

Referring to FIGS. 5 through 9, an alternate form of vial assembly of the present invention is there illustrated and generally identified by the numeral 102. The apparatus of this embodiment of the invention is similar in many respects to that shown in FIGS. 1 and 2 and includes a vial 104 having a fluid chamber 104a for containing the fluid to be added to the reservoir of a fluid dispenser or other fluid delivery device. As before the fluid can be a diluent or any of the medicaments or beneficial agents described in the previously identified U.S. Pat. No. 5,205,820.

The major difference between the vial assembly of this form of the invention and that shown in FIGS. 1 and 2 is that this latter form of the invention is specifically designed for use with needleless syringes have luer type connectors. Such syringes have recently become very popular due to needlestick problems experienced in using traditional needle type syringes.

As best seen in FIG. 5, vial 104 has open ends 104b and 104c and closely receives within chamber 104a a piston-like plunger 106 which is telescopically movable within chamber 104a from a first position, proximate the fill end 104b of the vial to a second position proximate opposite end 104c of the vial (see FIG. 9). Container 104 can be a glass vial, or a plastic vial, or any other suitable container that can be sterilized. Container 104 has an interior wall, the interior surface of which can be covered by covering means such as interfacial barrier materials or which can remain uncoated depending upon the base material used in constructing the container and depending upon the application to be made of the device. Containers of the type contemplated herein can be effectively used for very long-term storage. As shown in FIGS. 8 and 8A, the interior of the vial assembly of the embodiment of the invention there shown is covered by a thin laminate coating 105 which here comprises first, second and third layers 105a, 105b, and 105c. These layers cooperate to form a tailored barrier structure which alters the surface morphology of the vial and which can control the diffusion transport of water, water vapor and various gases. The materials used to form the layers can selectively comprise both rubber and glassy advanced polymers, including thermoplastic films such as polyvinylchloride (PVC), copolymers of vinylidene chloride and vinylchloride, polyethylene terephthalate (PET), tetrafluoroethylenehexafluoropropylene and vinylidene flouride (THV fluroplastic) ethylene, vinyl alcohol copolymers, advance polyesters, such as polyethylene naphthalene dicarboxylate, advance amorphous polymers, including polyvinyl chloride and polystyrene. Various oxygen barrier resins can also be used, including vinylidene chloride, aromatic nylon, amorphous nylon, polyacrylicimide and similar resins offered for sale by The Dow Chemical Company, Rohm & Hass and DuPont.

Surface coatings of the character here contemplated can include single or multiple layers of similar or different materials. The interfacial coating or coatings can be employed to increase the functional surface compatibility of the vial base material with the intended vial contents, the barrier properties of the vial base materials, including its gas permeation, migration and perm select characteristics and for optimizing the morphology of the internal vial material for specific applications.

Materials suitable for the construction of plastic vials include polycarbonate, high density polyethylene, polypropylene, nylon, polystyrene, polyamides, styrenes, and various like materials.

Also forming a part of the vial assembly of the present embodiment of the invention is an outer safety casing, shown here as comprising cooperating first and second portions 108a and 108b which are joined together to form a sterile barrier system. First portion 108a is provided with internal threads 110 and is closed by an externally threaded closure cap 112. Provided at its open end is a socket like construction 114 which is telescopically received within the open end portion 116 of second casing portion 108b. The outer casing is receivable over vial 104 and portions 108a and 108b are held in mating engagement by an overwrap 120 which functions as an interface sterility barrier and upon which appropriate identifying indicia 122 can be imprinted. A novel temperature indicator means, such as indicator "T" of the character previously described is also carried by overwrap 120. As shown in FIG. 5, a guide bead 124 is provided on portion 114. Bead 124 is receivable within a corresponding channel 126 provided in portion 108b to insure that portions 108a and 108b of the outer casing are properly aligned.

In a manner presently to be described, as the fluid chamber of the vial is filled with fluid using a needleless syringe "NS" (FIG. 7), piston 106 is moved within the vial by fluid pressure from the first position shown in FIG. 9 to a second position shown in FIG. 8 where it is disposed proximate end 104c. Piston 106 is provided with a plurality of circumferentially extending sealing beads 106a which sealably engage the inner walls 104d of container 104 as the piston moves internally thereof so as to prevent fluid leakage past the piston.

Referring now to FIGS. 6 and 8, after the vial assembly has been assembled in the manner shown in FIG. 8 and with cap 112 removed, the connector stem portion 130 of the syringe connector means is exposed to view (see FIG. 6). The syringe connector means of this form of the invention functions to interconnect the container with a needleless syringe of the character having a luer type receptacle adapted to receive a luer type connector "L" of the character provided at the terminal portion of the connector stem 130. The syringe connector means also comprises sealing means for sealing the inlet portion of vial 104. In the present form of the invention, the sealing means, in addition to connector stem 130, also includes inlet valve means for controlling fluid flow into chamber 104a. The inlet valve means here comprises a delivery stem 132 which terminates in a valve seat 134 (FIG. 5A). Disposed intermediate connector stem 130 and delivery stem 132, and integrally formed therewith, is a disk-like body portion 136 (FIG. 8). The various components of inlet valve means can be constructed of various dimensionally stable bondable materials, such as polycarbonate, polystyrene, nylon and various acrylic polymers.

As best seen by referring to FIG. 8, connector stem 130 has a central fluid passageway 130a while delivery stem 132 has a central fluid passageway 132a. The inlet valve means, in addition to valve seat 134, comprises a valve member 140 which is movable into sealable engagement with valve seat 134 in the manner shown in FIG. 8 so as to substantially block fluid flow through fluid passageway 132a. The inlet valve means of the present form of the invention also includes a valve housing 142 disposed adjacent delivery stem 132 for housing valve member 140 and for permitting movement of the valve member between the first substantially sealing position shown in FIG. 8 toward a second valve open position shown in FIG. 9. Valve housing 142 includes a cylindrical body portion 142a and a flange portion 142b. Cylindrical body portion 142a, which is adapted to telescopically receive delivery stem 132, is also provided with a fluid passageway 142c. With this construction, when the valve means of the invention is in the open position shown in FIG. 9, fluid can flow through the connector means, past the valve member 140, through passageway 142c, and into the interior chamber 104a of container 104. When chamber 104a is filled, fluid pressure within the chamber will cause the valve to return to a closed position.

The sealing means of the invention which functions to close first end 104b of container 104, further includes an elastomeric plug-like member 146 having a central bore 146a, a generally cylindrically shaped body portion 146b, and an enlarged diameter flange portion 146c (FIGS. 5 and 8). Suitable materials for member 146 include silicone rubber, butyl rubber, butylpolyisoprene blend, ethylenepropylene elastomers, or any other elastomeric material compatible with the vial contents. As shown in FIG. 8, cylindrical portion 146b fits snugly within vial 104 and in cooperation with connector stem 130, valve housing 142, and valve member 140, functions to sealably close end 104b of container 104. To maintain the aforementioned components in position within container 104, interconnection means are provided which here take the form of a crimp cap 150 having a skirt portion 150a, the periphery 150b of which can be crimped inwardly into an annular groove 152 which is provided in container 104 (FIG. 8). Crimp cap 150 can be constructed from a variety of malleable materials including aluminium, stainless steel and like materials. Disposed between flange 150c of the crimp cap and body portion 136 of the connector means is an elastomeric annular-shaped crimp seal 154. In engagement with the opposing face of the flange 150 is an interior partition wall 158 formed in portion 108a of the outer safety casing. When closure cap 112 is threadably connected with portion 108a in the manner shown in FIG. 8, the inner edge of the cap is in close proximity with wall 158 and a centrally disposed cylindrical extension 160 formed on cap 112 is telescopically received within passageway 130a of connector stem 130.

In filling the vial assembly, cap 112 is removed and syringe "NS" is interconnected with the connector stem 130 in the manner shown in FIGS. 7 and 9 so that luer connector "L" is securely locked within the syringe receptacle. As fluid is forced from the syringe into passageways 130a and 132a, valve member 140 will be moved away from seat 134 and fluid will flow toward chamber 104a of the container and will impinge on plunger 106. The fluid impinging on the plunger 106, will force it to the left until it moves into close proximity with end 104c of the vial where it engages a retainer ring 162 (FIG. 9) that is closely received within end 104c of the vial. During the vial filling step, air disposed within chamber 104c will be expelled through a sterile vent patch 164 which is bonded to a closure cap 166 that is provided with vent apertures 166a. Vent patch 164 can be constructed from a gas permeable hydrophobic material such as expanded polytetrafluoroethylene (PTFE) membrane or an acrylic copolymer membrane on a nonwoven support.

After the vial has been filled with the selected fluid, cap 112 is reconnected with the outer casing 108 so as to maintain the interior of the vial in a sealed, aseptic and sterile condition. As best seen in FIG. 5, casing portions 108a and 108b is provided with an elongated viewing slot 170 that permits viewing of the interior chamber 104a of the vial. Similarly, overwrap 120 has an elongated viewing slot 172 which is indexable with slot 170. With this construction, the user can tell at a glance whether the vial is full, partially full, or empty.

In its sealed, aseptic condition with a sterile fluid path, vial assembly 102 can be stored as may be necessary until it is to be used to fill a reservoir of a fluid dispenser of a delivery apparatus such as that shown in FIGS. 34 and 35 of U.S. Ser. No. 08/069,937.

Turning now to FIGS. 10 through 14, still another form of the vial assembly of the present invention is there shown. This embodiment is similar in many respects to that shown in FIGS. 5 through 9 save that the vial or fluid chamber is constructed of plastic and is non-circular in cross section. Like numerals have been used in FIGS. 10 through 14 to identify like components.

Figure 10:
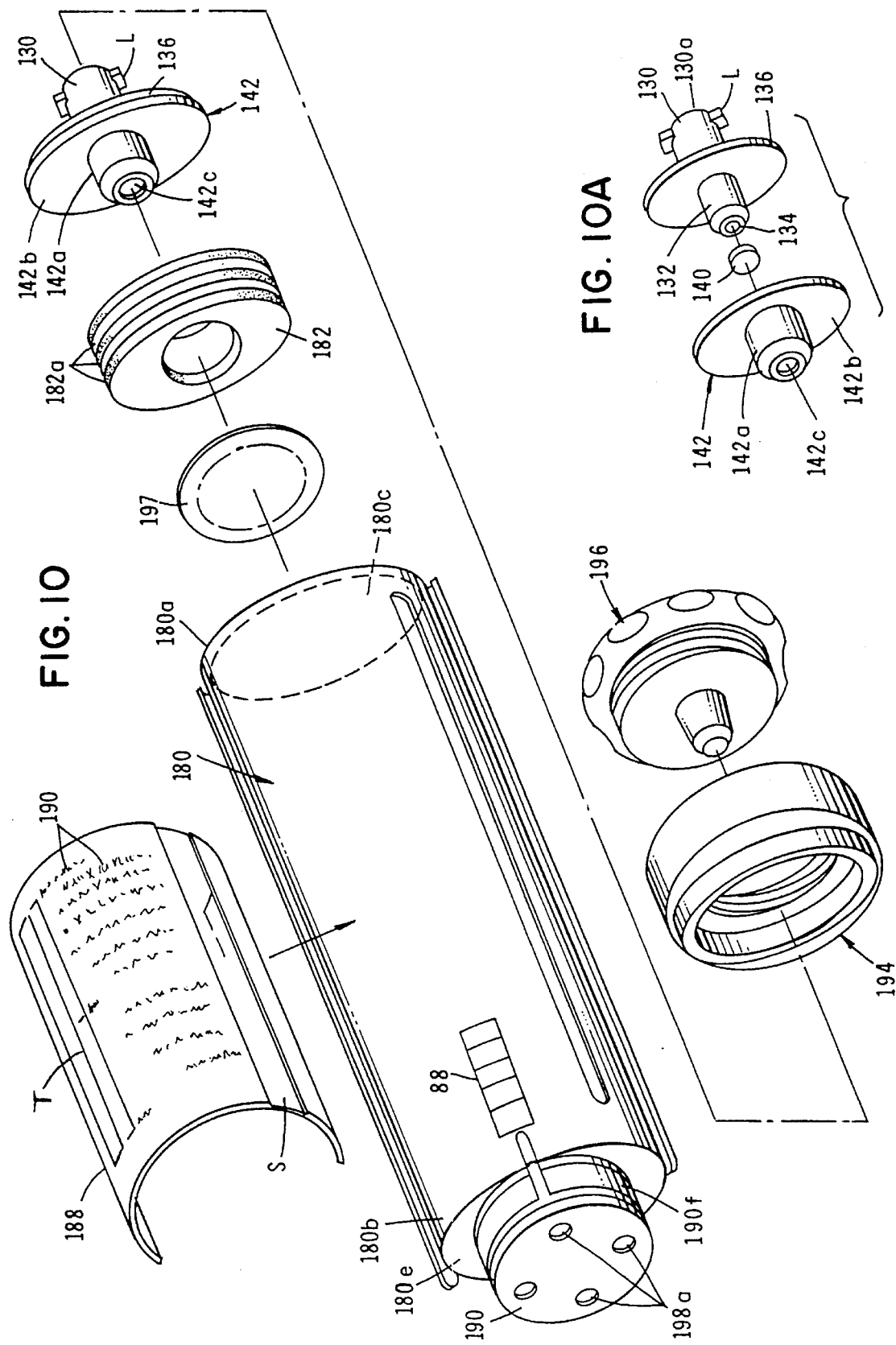
FIG. 10 is a generally perspective, exploded view of yet another form of the field filled vial assembly of the present invention.
Figure 11:
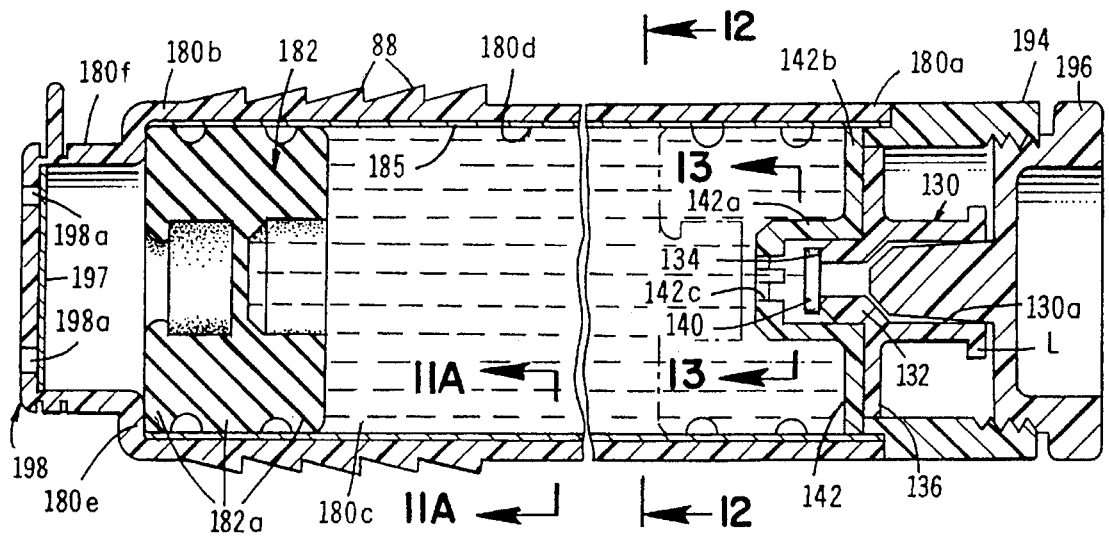
FIG. 11 is an enlarged, foreshortened, cross-sectional side view of the vial assembly of FIG. 10.
Figure 12:
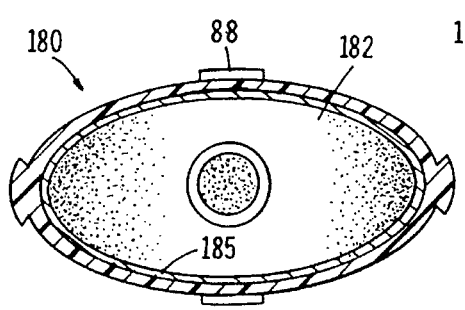
FIG. 12 is a cross-sectional view taken along lines 12—12 of FIG. 11.
Figure 11A:
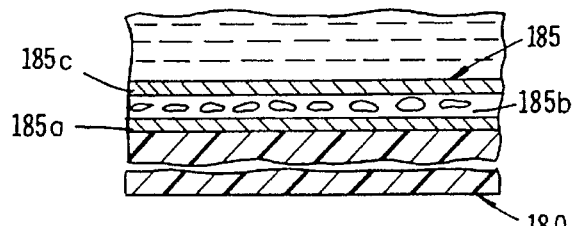
FIG. 11A is an enlarged cross-sectional view taken along lines 11A—11A of FIG. 11.
Figure 13:
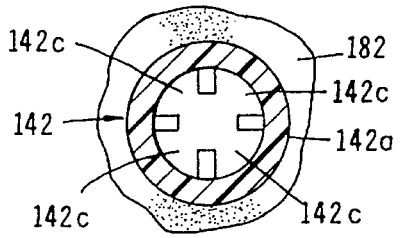
FIG. 13 is a cross-sectional view taken along lines 13—13 of FIG. 11.

As best seen in FIGS. 10 and 11, the apparatus of this latest form of the invention comprises a fluid container 180 having end portions 180a and 180b and closely receives within a chamber 180c a piston-like plunger 182 which is telescopically movable within chamber 180c from a first position, proximate the fill end 180a of the container to a second position proximate opposite end 180b of the container (see FIG. 11). As previously mentioned, container 180 is formed of plastic and, as shown in FIG. 12, is generally elliptical in cross section. The interior surface of the container can be coated or uncoated depending upon the material used in constructing the container and depending upon the use to be made of the device. As shown in FIGS. 11, 11A and 12, the interior of the container of the embodiment of the invention there shown is covered with a thin laminate interfacial structure 185 made up of layers 185a, 185b, and 185c. These layers are of the general character of layers 105 as previously described in connection with the embodiment of the invention shown in FIGS. 7 and 8 and can be formed of materials of the type previously identified herein. It is to be understood that for some applications, only a single layer coating, such as a plasma deposited facing surface, having vapor barrier properties, can be used.

Also forming a part of the vial assembly of this latest embodiment of the invention is an overwrap 188 which surrounds container 180 and functions as a medicament instruction label upon which appropriate identifying indicia 190 can be imprinted. As before, a novel temperature indicator means, such as indicator "T", of the character previously described is also carried by overwrap 188.

Figure 14:
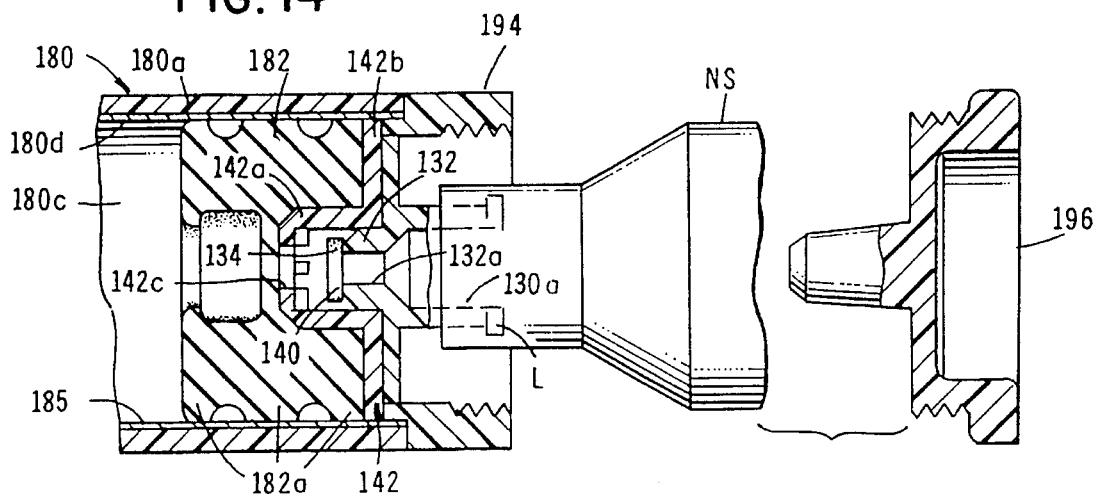
FIG. 14 is a fragmentary, cross-sectional exploded view of the fill end portion of the assembly showing the removal of the end cap and the interconnection of a syringe with the fill end portion.

As was the case with the embodiment of the invention shown in FIGS. 5 through 10, the fluid chamber of the container is filled with fluid using a needleless syringe "NS" (FIG. 14). As the chamber is filled, piston 182 is moved within the vial by fluid pressure from the first position shown in phantom lines in FIG. 11 to a second position shown by the solid lines in FIG. 11 where it is disposed proximate end 180b. Piston 182, which is generally elliptical in cross section, is provided with a plurality of circumferentially extending sealing beads 182a which sealably engage the inner walls 180d of container 180 as the piston moves internally thereof so as to prevent fluid leakage past the piston.

Referring particularly to FIGS. 11 and 14, an internally threaded cap adapter 194 is affixed to end 180a of container 180 by any suitable means such as sonic bonding. Adapter 194 is generally circular in cross section at any point and functions to receive an externally threaded closure cap 196.

Mounted within adapter 194 is the sealing means of this form of the invention, which is substantially identical to that previously described and functions to seal the inlet of the vial chamber and also functions to interconnect the container with a needleless syringe of the type having a luer type receptacle. As before, the connector stem 130 is provided with a luer type connector "L" which is lockably received within the syringe receptacle in the manner shown in FIG. 14. The connector means, in addition to connector stem 130, also comprises a delivery stem 132 which terminates in a valve seat 134. Disposed intermediate connector stem 130 and delivery stem 132, and integrally formed therewith, is a disk-like body portion 136.

As best seen by referring to FIGS. 10 and 11, connector stem 130 has a central fluid passageway 130a while delivery stem 132 has a central fluid passageway 132a. The sealing means also includes inlet valve means for controlling fluid flow into the vial chamber. This valve means is also similar to the previously described valve means and comprises a valve member 140 which is movable into sealable engagement with valve seat 134 in the manner shown in FIG. 11 so as to block fluid flow through fluid passageway 132a. The valve means of this latest form of the invention also includes a valve housing 142 disposed adjacent delivery stem 132 for housing valve member 140 and for permitting movement of the valve member between the first sealing position shown in FIG. 11 toward a second valve open position shown in FIG. 10A. Valve housing 142 includes a cylindrical body portion 142a and a flange portion 142b. Cylindrical body portion 142a, which is adapted to telescopically receive delivery stem 132, is also provided with a fluid passageway 142c. With this construction, when the valve means of the invention is in the open position, fluid can flow through the connector means, past the valve member 140, through passageway 142c, and into the interior chamber 180c of container 180. When the chamber is filled, fluid pressure within the chamber will cause the valve to return to its closed position.

To close first end 180a of container 180, closure cap 196 is threadably connected to an annular threaded portion or cap adapter 194 in the manner shown in FIG. 11.

In filling container 180, cap 196 is removed in the manner shown in FIG. 14 and syringe "NS" is interconnected with the connector stem 130 so that luer connector "L" is securely locked within the syringe receptacle. As fluid is forced from the syringe into passageways 130a and 132a, elastomeric valve member 140 will be moved away from seat 134 and fluid will flow toward chamber 180c of the container and will impinge on plunger 182. The fluid impinging on the plunger 182 will force it to the left until it moves into close proximity with end 180b of the vial where it engages a step 180e formed in container 180 at the junction of the main body of the container and a reduced diameter portion 180f. During the vial filling step, air disposed within chamber 180c will be expelled through a sterile vent patch 197 which is of the same character as the previously described hydrophobic vent patch 164, which is bonded to a closure cap 198 that is provided with vent apertures 198a. Closure cap 198 functions to close the end of reduced diameter portion 180f (FIG. 10).

After the vial has been filled with the selected fluid, cap 196 is reconnected to the container so as to maintain the interior thereof in a sealed, aseptic condition. As best seen in FIG. 10, overwrap 188 is provided with an elongated viewing slot "S" that permits viewing of the interior chamber of the container.

As is the case with the earlier described embodiments, when the container is in its sealed, sterile fluid path condition, it can be stored as may be necessary until it is to be used to fill a fluid dispenser or a reservoir of a delivery apparatus such as that shown in FIGS. 34 and 35 of U.S. Ser. No. 08/069,937.

Turning now to FIG. 15 through 19, another form of the vial assembly of the present invention is there shown. This embodiment is similar in many respects to that shown in FIGS. 5 through 9 save that the fluid chamber of the vial assembly is filled by a syringe having a blunt cannula rather than a luer type connector. Like numerals have been used in FIGS. 15 through 19 to identify like components.

Figure 16:
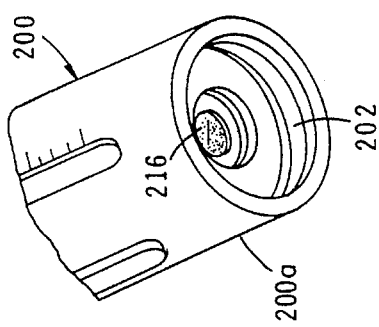
FIG. 16 is a fragmentary, generally perspective view of one end portion of the vial assembly shown in FIG. 15.
Figure 15:
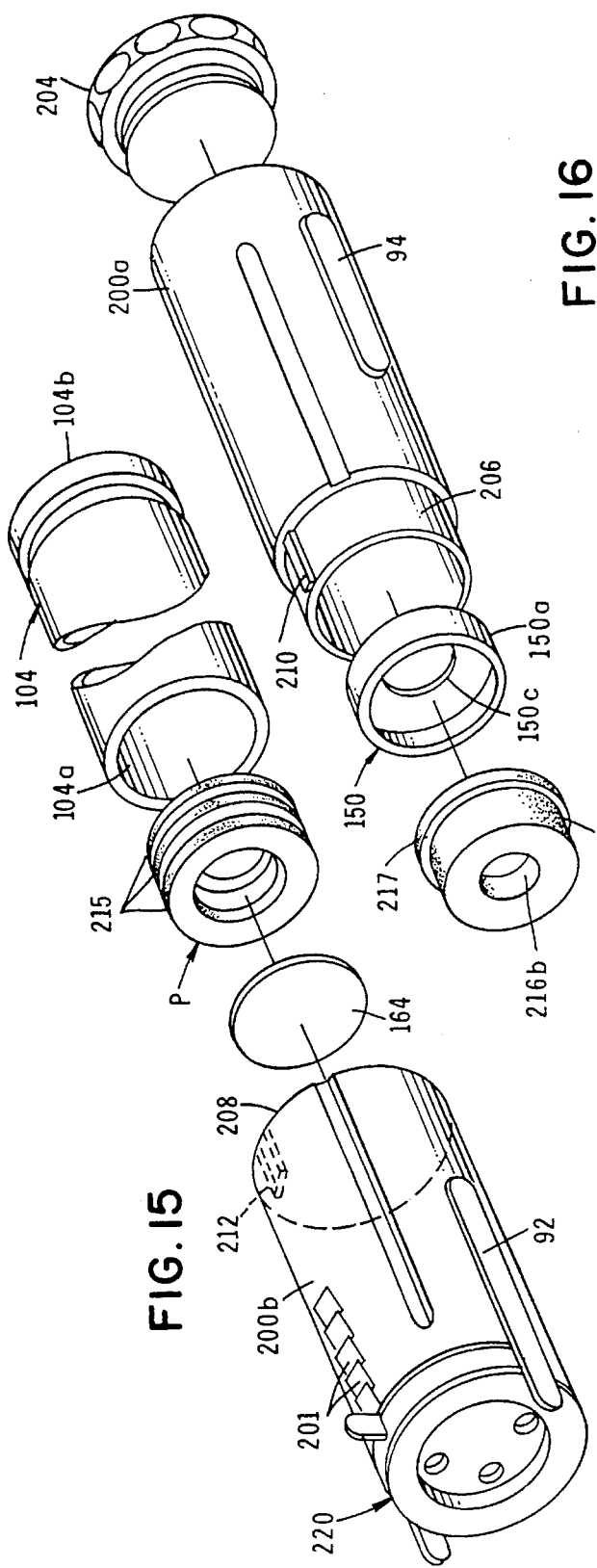
FIG. 15 is a generally perspective, exploded view of another form of the field filled vial assembly of the present invention which is adapted to be filled by a blunt cannula.
Figure 17:
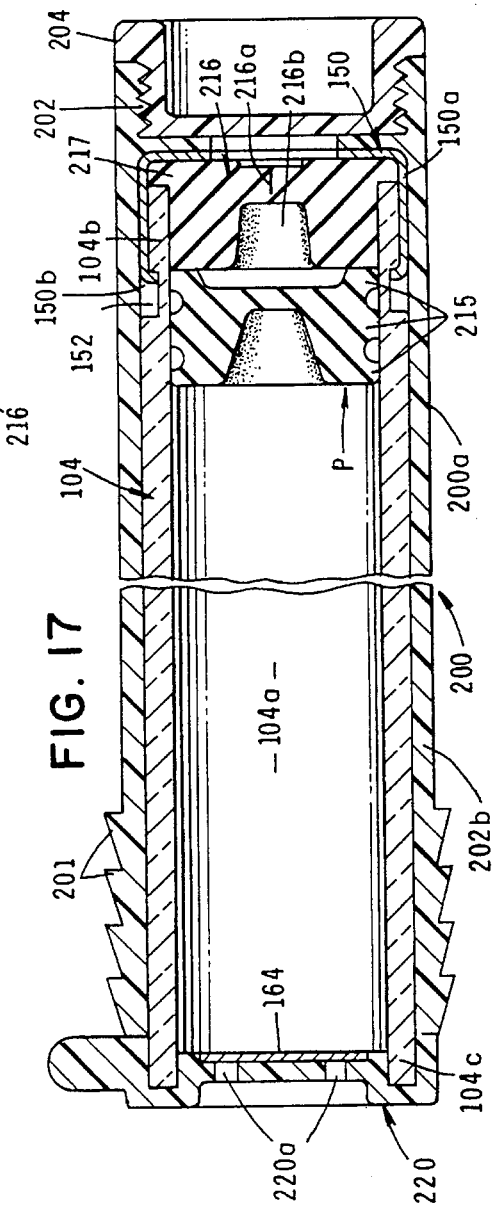
FIG. 17 is an enlarged, cross-sectional side view of the vial assembly shown in FIG. 15.

As best seen in FIGS. 15 through 17, vial 104 has a chamber 104a within which a piston-like plunger P is telescopically movable from a first position, proximate the fill end 104b of the vial to a second position proximate opposite end 104c of the vial (see FIG. 17). Container 104 can be a glass vial, or a plastic vial, or any other container suitable for the intended end use. Container 104 has an interior wall, the interior surface of which can be covered by covering means such as interfacial barrier materials or which can remain uncoated depending upon the base material used in constructing the container and depending upon the application to be made of the device.

Also forming a part of the vial assembly of this embodiment of the invention is an outer safety casing 200, shown here as comprising cooperating first and second portions 200a and 200b which are joined together to form a sterile barrier system. First portion 200a is provided with internal threads 202 and is closed by an externally threaded closure cap 204. Provided at its open end is a socket like construction 206 which is telescopically received within the open end portion 208 of second casing portion 200b. Outer casing 200 is receivable over vial 104 and portions 200a and 200b are held in mating engagement by any suitable means such as bonding or by an overwrap of the character previously described which functions as an interface sterility barrier and upon which appropriate identifying indicia can be imprinted (see, for example, overwrap 120). As shown in FIG. 15, a guide bead 210 is provided on portion 206. Bead 210 is receivable within a corresponding channel 212 provided in portion 200b to insure that portions 200a and 200b are properly aligned.

Figure 18:
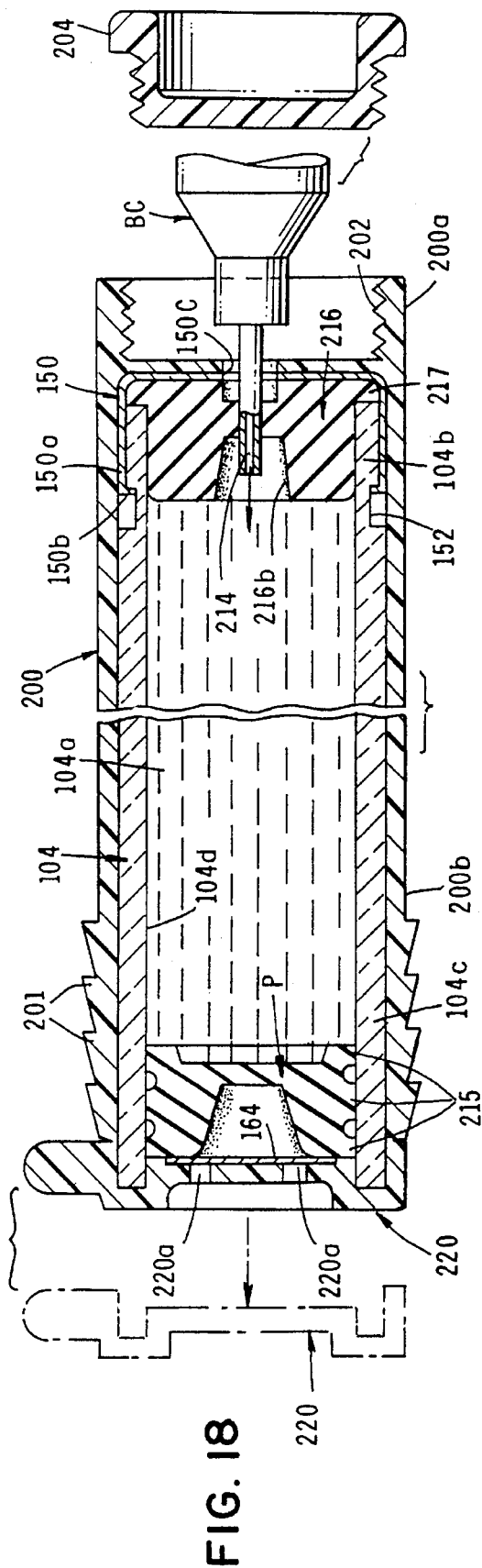
FIG. 18 is an enlarged cross-sectional view of the device of the invention shown in FIG. 17 with the cap having been removed and the fluid chamber having been filled with a syringe provided with a blunt cannula.

In a manner presently to be described, as the fluid chamber of the vial is filled with fluid using a syringe "BC" having a blunt cannula 214 (FIG. 18), plunger "P" is moved within the vial by fluid pressure from the first position shown in FIG. 17 to a second position shown in FIG. 18 where it is disposed proximate end 104c. Plunger "P" is provided with a plurality of circumferentially extending sealing beads 215 which sealably engage the inner walls 104d of container 104 as the piston moves internally thereof so as to prevent fluid leakage past the piston.

Referring now to FIGS. 17 and 18, after the vial assembly has been assembled in the manner shown and with cap 204 removed, a slit septum closure means 216 is exposed to view (see FIG. 18). Slit septum 216 is constructed from any suitable elastomeric material and is provided with a slit 216a which receives blunt cannula 214 of syringe "BC". During the filling step, septum 216 sealably closes end 104b of vial 104 and sealably engages the blunt cannula to prevent leakage between the cannula and the slit septum.

To maintain septum 216 in position within container 104, interconnection means are provided which here take the form of the previously identified crimp cap 150 having a skirt portion 150a, the periphery 150b of which can be crimped inwardly into an annular groove 152 which is provided in container 104 (FIG. 17). Enlarged diameter flange portion 217 of septum 216 is maintained in engagement with the end of vial 104 by the crimp cap so as to sealably interconnect the septum with the vial. Crimp cap 150 is also provided with a central opening 150c to receive the blunt cannula during the vial filling step.

In filling the vial assembly, cap 204 is removed and cannula 214 of syringe "BC" is inserted into slit septum 216 in the manner shown in FIG. 18. As fluid is forced from the syringe into a cavity 216b provided in the septum, fluid will impinge on plunger "P" forcing it to the left until it moves into close proximity with end 104c of the vial where it engages a vented closure cap 220 that closes end 104c of the vial. During the vial filling step, air disposed within chamber 104a will be expelled through a sterile vent patch 164 of the character previously described which is bonded to a closure cap 220. Cap 220 is provided with vent apertures 220a to permit free passage of gas through the apertures.

After the vial has been filled with the selected fluid, cap 204 is reconnected with the outer casing 200 so as to maintain the interior of the vial in a sealed, aseptic and sterile condition. In its sealed, aseptic condition, the vial assembly can be stored as may be necessary until it is to be used to fill the reservoir of a platform-mounted fluid dispenser of the general character shown in FIG. 23 of U.S. Ser. No. 08/129,693. The fluid dispenser, which is identified in FIG. 19 by the numeral 225, is provided with a vial receiving opening 225a which, after tear-away cap 220 has been removed, closely receives end portion 200b in the manner shown in FIG. 19. Dispenser 225 includes internally disposed tabs 227 that matably engage locking tabs 201 provided in casing 200 so that once the vial assembly is fully mated with the dispenser it cannot be removed.

Figure 19:
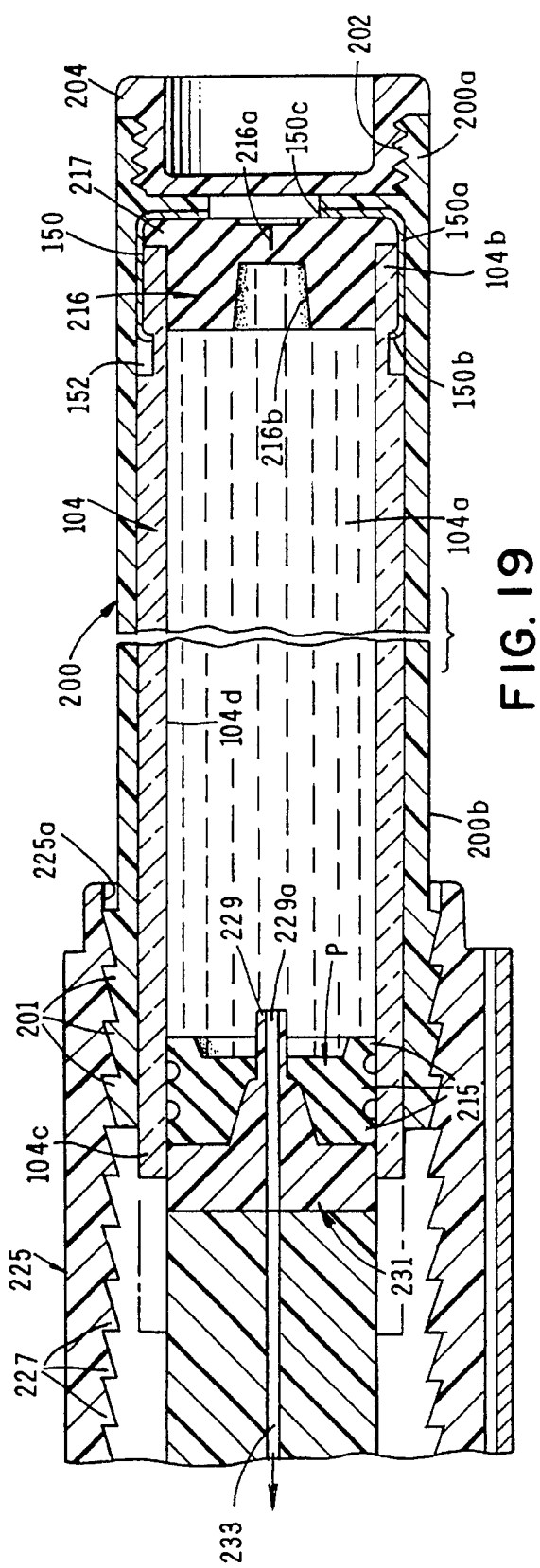
FIG. 19 is a cross-sectional view similar to FIG. 18, but showing the vial assembly mated with a fluid dispenser also having a blunt cannula.

As indicated in FIG. 19, fluid dispenser 225 is provided proximate opening 225a with a blunt cannula 229 which has a fluid passageway 229a. Cannula 229 is held in position by a support member 231 so that passageway 229a is in communication with the fluid reservoirs of the dispenser via a fluid passageway 233. Reference should be made to Ser. No. 08/129,693 for the details of the construction of the fluid dispenser and the manner of its interconnection with cardet-like support platforms.

Turning now to FIGS. 20 through 23, yet another form of the vial assembly of the present invention is there shown. This embodiment is similar in most respects to that just discussed and shown in FIGS. 15 through 19 save that the telescopically movable plunger of the vial assembly is provided with outlet valve means that are operable by an operating member provided within the platform-mountable fluid dispenser.

As best seen in FIGS. 20 and 21, vial 250 has a chamber 250a within which a piston-like plunger 252, is telescopically movable from a first position proximate the fill end 250b of the vial to a second position proximate opposite end 250c of the vial (see FIG. 22). As before, vial 250 can be a glass vial, or a plastic vial or any other suitable container.

Also forming a part of the vial assembly of this embodiment of the invention is an outer safety casing 254, shown here as comprising cooperating first and second portions 254a and 254b which are joined together to form a sterile barrier system. First portion 254a is provided with internal threads 256 and is closed by an externally threaded closure cap 258. Provided at its open end is a socket-like construction 260 which, as previously described, is telescopically received within the open end portion of the second casing portion. Outer casing 254 is receivable over vial 250 and portions 254a and 254b are held in mating engagement by any suitable means such as bonding or by an overwrap of the character previously described which functions as an interface sterility barrier and upon which appropriate identifying indicia can be imprinted (see, for example, overwrap 120 shown in FIG. 5).

As was the case with the embodiment shown in FIGS. 15 through 19, the fluid chamber of the vial is filled with fluid using a syringe "BC" having a blunt cannula 214 (FIG. 22), plunger 252 is moved within the vial by fluid pressure from the first position shown in FIG. 21 to a second position shown in FIG. 22 where it is disposed proximate end 250c. Plunger 252 is provided with a plurality of circumferentially extending sealing beads 260 which sealably engage the inner walls 250d of container 250 as the piston moves internally thereof so as to prevent fluid leakage past the piston.

Referring now to FIGS. 21 and 22, after the vial assembly has been assembled in the manner shown and with cap 258 removed, a septum 262 is exposed to view. Septum 262 of the sealing means of the invention is constructed from any suitable elastomeric material and is provided with a wall portion 262a formed of a non-coring elastomeric that includes a recess 263 which receives blunt cannula 214 of syringe "BC". During the filling step, septum 262 sealably closes end 250b of vial 250 and sealably engages the blunt cannula to prevent leakage between the cannula and the septum.

To maintain septum 262 in position within container 250, interconnection means are provided which here take the form of a crimp cap 266 having a skirt portion 266a, the periphery 266b of which can be crimped inwardly into an annular groove 267 which is provided in container 250 (FIG. 21). Enlarged diameter flange portion 262a of septum 262 is maintained in engagement with the end of vial 250 by the crimp cap so as to sealably interconnect the septum with the vial. Crimp cap 266 is also provided with a central opening 266c to receive the blunt cannula during the vial filling step.

In filling the vial assembly, cap 258 is removed and cannula 214 of syringe "BC" is inserted into wall 262a in the manner shown in FIG. 22. As fluid is forced from the syringe into a cavity 268 provided in the septum, fluid will impinge on plunger 252 forcing it to the left until it moves into close proximity with end 250c of the vial where it engages an elastomeric O ring which is supported by a shoulder 270 formed on casing 254b. An elastomeric O-ring rests against shoulder 270 for engagement with the outlet end of vial 250. During the vial filling step, air disposed within chamber 250a will be expelled through a sterile vent patch 164 of the character previously described which is bonded to an inside surface of end wall 220. Portion 254d is integrally formed with casing 254b and includes an end wall 220 which is provided with vent apertures 220a that permits free passage of vent gases.

After the vial has been filled with the selected fluid, cap 258 is reconnected with the outer casing 254a so as to maintain the interior of the vial in a sealed, aseptic and sterile condition. In its filled and sealed, aseptic condition, the vial assembly can be stored as may be necessary until it is to be used to fill the reservoir of a fluid dispenser 273 having an inlet portion as depicted in FIG. 23 and being of the general character described in U.S. Ser. No. 08/129,693. Referring to FIG. 23, dispenser 273 is provided with a vial receiving opening 273a which closely receives end portion 254b in the manner shown in FIG. 23. Dispenser 273 includes internally disposed tabs 275 that matably engage locking tabs 255 provided on casing 254 so that once the vial assembly is fully mated with the dispenser it cannot be removed.

As indicated in FIGS. 23, 24, and 25, dispenser 273 is provided proximate opening 273a with valve operating means, here shown as member 277, which has a fluid passageway 277a. Operating member 277 is held in position within opening 273a so that when the vial assembly is mated with the fluid dispenser, passageway 277a will communicate with central fluid passageway 252a provided in plunger 252 (see FIG. 23). Passageway 252a is normally closed by outlet valve means, shown here as a valve member 280, which includes a generally disk shaped portion 280a and a stem portion 280b which is generally cross-shaped in cross section (FIG. 24). Portion 280a is closely receivable within a counter bore 252b provided in plunger 252 so that when the valve means is closed as shown in FIG. 22, fluid flow between vial chamber 250a and fluid passageway 252a will be substantially sealed. As indicated in FIG. 23, when the vial assembly is mated with fluid dispenser 273, portion 277b of operating member 277 will urge valve member 280 to the right, or inwardly of vial chamber 250a, thereby opening the valve and permitting fluid flow from chamber 250a into passageway 277a and then toward the fluid reservoirs of the fluid dispenser. Once again, reference should be had to Ser. No. 08/129,693 for the details of the construction of one form of fluid dispenser usable with this latest embodiment of the invention.

Referring to FIGS. 26 through 31, another form of vial assembly of the present invention is there illustrated and generally identified by the numeral 300. The apparatus of this embodiment of the invention is similar in many respects to that shown in FIGS. 15 through 19 and like numerals are used to identify like components.

The principal difference between this latest embodiment and those earlier described relate to the design of the filling mechanism and the design of the telescopically movable plunger of the vial assembly.

As best seen in FIGS. 26 and 27, vial 104, which is of the character previously described, has a chamber 104a within which a piston-like plunger 302 is telescopically movable from a first position, proximate the fill end 104b of the vial to a second position proximate opposite end 104c of the vial (see FIG. 29). As before, container 104 can be a glass vial, or a plastic vial, or any other suitable container that can be sterilized. Container 104 has an interior wall, the interior surface of which can be covered by covering means such as the interfacial barrier materials previously described or the interior wall can remain uncoated depending upon the base material used in constructing the container and depending upon the application to be made of the device.

Also forming apart of the vial assembly of this embodiment of the invention is an outer safety casing 254 of the character shown in FIG. 21 and as earlier described herein which functions to provide a sterile barrier system. First portion 254a of the safety casing is provided with internal threads 202 and is closed by an externally threaded closure cap 303. As shown in FIG. 28, casing 254 is receivable over vial 104 and portions 254a and 254b are held in mating engagement by any suitable means such as bonding or by an overwrap of the character previously described which functions as an interface sterility barrier and upon which appropriate identifying indicia can be imprinted (see, for example, overwrap 120 FIG. 5).

In a manner presently to be described, as the fluid chamber of the vial is filled with fluid using a slip fit, luer type syringe "SF" or other appropriate filing means, plunger 302 is moved within the vial by fluid pressure from the first position shown in FIG. 28 to a second position shown in FIG. 29 where it is disposed proximate end 104c. As before, plunger 302, which is here provided in the form of a duck-bill type valve, has a plurality of circumferentially extending sealing beads 304 which sealably engage the inner wall 104d of container 104 as the piston moves internally thereof so as to prevent fluid leakage past the piston.

Referring now to FIGS. 28 and 29, after the vial assembly has been assembled in the manner shown and with cap 303 removed, the sealing means, including fill assembly 306, is exposed to view (see FIG. 27). Fill assembly 306, which includes the inlet valve means, comprises a valve seat member 308 having a slip-fit luer receiving nipple 310, a valve housing 312 and a valve member 314. Fill assembly 306, which also includes annular seal members 316 and 317 is held in position within casing 254a by interconnection means comprising the previously identified crimp cap 150. Cap 150 includes a skirt portion 150a, the periphery 150b of which can be crimped inwardly into an annular groove 152 which is provided in container 104 (FIG. 28). Crimp cap 150 is also provided with a central opening 150c to receive nipple 310 so as to permit interconnection of syringe "SF" after cap 303 has been removed.

Following interconnection of the slip-fit syringe with nipple 310 in the manner shown in FIG. 29, fluid can be forced from the syringe into a central fluid passageway 318 provided in nipple 310. Fluid flowing through passageway 318 under pressure will cause valve member 314 to move away from valve seat 308a and into engagement with the inboard portion 312a of valve housing 312 (FIG. 29). This permits fluid to flow into chamber 104a of vial 104. Due to the novel construction of the valve means, or duck-bill type plunger 302, "bill" portions 302a will remain closed and plunger 302 will move to the left toward end 104c of the vial where it engages shoulder 270 of casing 254 (FIG. 29). During the vial filling step, air disposed within chamber 104a will be expelled through a sterile vent patch 164 of the character previously described which is bonded to a closure cap 220. Cap 220 is provided with vent apertures 220a to permit free passage of gas.

After the vial has been filled with the selected fluid, cap 303 is reconnected with the outer casing 254 so as to maintain the interior of the vial in a sealed, aseptic and sterile condition. In its sealed, aseptic condition, the vial assembly can be stored as may be necessary until it is to be used to fill the reservoir of a platform-mounted fluid dispenser. The fluid dispenser, which is identified in FIG. 30 by the numeral 325, is provided with a vial receiving opening 325a which closely receives end portion 254b in the manner shown in FIG. 30. Dispenser 325 includes internally disposed tabs 227 that matably engage locking tabs 255 provided on casing 254 so that once the vial assembly is fully mated with the dispenser it cannot be removed.

As indicated in FIG. 30, fluid dispenser 325 is provided proximate opening 325a with a valve opening member 328 which has a fluid passageway 328a. Member 328 is held in position by a support member 330 so that passageway 328a is in communication with a central passageway 330a provided in support 330 that is in communication with the fluid reservoirs of the dispenser. Once again, reference should be made to Ser. No. 08/129,693 for the details of the construction of the fluid dispenser and the manner of its interconnection with cardet-like support platforms or with similar supports.

After tear-away cap 220 is removed and as the vial assembly is mated with fluid dispenser 325 in the manner shown in FIG. 30, valve opening member 328 will move between the "bill" portions 302a of the duck-bill type valve thereby permitting fluid to flow from chamber 104a into passageway 328a, then into passageway 330a and finally into the reservoir of the fluid dispenser 325.

Turning now to FIGS. 32 through 33, yet another form of the vial assembly of the present invention is there shown. This embodiment which is generally designated by the numeral 350 is similar in most respects to the embodiment just discussed and shown in FIGS. 26 through 31, save that the telescopically movable plunger of the vial assembly, rather than being a duck-bill type valve member, is provided with internal outlet valve means that are operable by an operating member provided within a fluid dispenser of the character shown in FIG. 33. Like members are used in FIGS. 32 through 40 to identify like components.

As indicated in FIGS. 32 through 36, vial assembly 350, if filled in the manner previously described, by a slip-fit syringe "SF". Because the sealing and inlet valve means of this form of the invention as well as their method of operation is the same as previously described, the filling step will not be further discussed at this time.

During filling, a piston-like plunger assembly 352 is telescopically movable from a first position, proximate the fill end 104b of the vial to a second position proximate opposite end 104c of the vial (see FIG. 36). As best seen in FIGS. 37 and 38, plunger assembly 352 here comprises an elastomeric member 354 having a central passageway 354a and a plurality of circumferentially extending sealing beads 354b which sealably engage the inner wall 104d of vial 104. Mounted within passageway 354a is an outlet valve means which comprises a valve seat member 356 having a valve seat 356a and a valve member 358 which is movable toward and away from the valve seat in a manner presently to be described. Also comprising a part of the outlet valve means is a locking member 360 which is disposed within passageway 354a. Member 360 has a flange portion 360a which is received within an annular groove 354c provided member 354 (FIG. 38) and lockably engages an annular protuberance 356b which is formed on valve seat member 356 and which also extends into groove 354c. A skirt like portion 356c extends from protuberance 356b and includes an inboard edge 356d that sealably engages an elastomeric seal 361 carried by the fluid dispenser when the vial assembly is mated with the fluid dispenser.

After the vial has been filled with the selected fluid, cap 303 is reconnected with the outer casing 254a so as to maintain the interior of the vial in a sealed, aseptic condition. In its sealed, aseptic condition, the vial assembly can be stored as may be necessary until it is to be used to fill the reservoir of a fluid dispenser of the general character shown in FIG. 33. The fluid dispenser, which is identified in FIGS. 33 and 37 by the numeral 365, is provided with a vial receiving opening 365a which closely receives end portion 254b in the manner shown in FIGS. 33 and 37. As before, dispenser 365 includes internally disposed tabs 275 that matably engage locking tabs 255 provided on casing 254 so that once the vial assembly is fully mated with the dispenser it cannot be removed.

As indicated in FIGS. 37 through 40, dispenser 365 is provided proximate opening 365a with valve operating means, shown here as a member 367 which has a fluid passageway 367a. Operating member 367 is held in position within opening 365a so that when the vial assembly is mated with the fluid dispenser, operating member 367 will be received within skirt portion 356c of member 356 so that passageway 367a will communicate with vial chamber 104a when the outlet valve means is opened in the manner shown in FIG. 38. As indicated in FIG. 38, when the vial assembly is mated with fluid dispenser 365, operating member 367 will urge valve member 358 to the right, or inwardly toward vial chamber 104a, thereby opening the valve and permitting fluid flow from chamber 104a, between legs 367b provided on member 367 (FIG. 40), into passageway 367a and then toward the fluid reservoirs of the fluid dispenser.

Turning next to FIGS. 41 through 47, yet another alternate form of vial assembly of the present invention is there illustrated and generally identified by the numeral 400. The apparatus of this embodiment of the invention is similar in many respects to that shown in FIGS. 35, 36, and 37, but includes fluid inlet and outlet valve means of a slightly different construction. As before, the vial assembly includes a vial 104 having a fluid chamber 104a for containing the fluid to be added to the reservoir of a fluid dispenser or other fluid delivery device. Surrounding vial 104 is an outer casing 402 having end portions 402a and 402b. Because of the similarly of this embodiment to those previously described, like numerals are used where appropriate to identify like components.

As was the case with the embodiment of the invention shown in FIGS. 5 through 9, the fluid chamber of the vial is filled with fluid using a needleless syringe "NS" having a conventional luer connector. In a manner presently to be described, as the fluid chamber is filled, a plunger assembly 404 is moved from the position shown in FIG. 42 toward the position shown in FIG. 43.

Plunger assembly 404 here comprises an elastomeric member 406 having a central passageway 406a and a plurality of circumferentially extending sealing beads 406b which sealably engage the inner wall 104d of vial 104. Mounted within passageway 406a is an outlet valve means which comprises a valve seat member 408 having a valve seat 408a and a valve member 410 which is movable toward and away from the valve seat in a manner presently to be described. Also comprising a part of the outlet valve means is a locking member 412 which is disposed within passageway 406a. Member 412 has a flange portion 412a which is received within an annular groove 406c provided in member 406 (FIG. 46) and lockably engages an annular protuberance 408b which is formed on valve seat member 408 and which also extends into groove 406c. A skirt like portion 408c extends from protuberance 408b and includes an inboard edge 408d that sealably engages an elastomeric seal 415 carried by the fluid dispenser when the vial assembly is mated with the fluid dispenser in a manner presently to be described.

For filling the fluid chamber of the vial, a syringe connector means is provided in the form of a connector stem 418 that includes a luer type connector "L" which is lockably received within the syringe receptacle in the manner shown in FIG. 43. Connector stem 418 comprises a part of the sealing means of this embodiment of the invention which assembly includes inlet or fill valve means, including a valve housing 421, as well as annular seal members 422 and 424 all of which are held in position within casing 402 by interconnection means comprising the previously identified crimp cap 150.

The sealing means of this latest form of the invention includes an inlet valve means which comprises a valve seat member 428, the forward portion of which includes the previously identified connector stem 418. The rearward portion of member 428 includes a disk-like protuberance 428a and a skirt portion 428b that extends therefrom. Disposed interiorly of skirt portion 428b is a valve seat 428c.

A cylindrical valve member 430, which also forms a part of the fill valve means, is movable within skirt portion 428b from a closed position wherein it sealably engages seat 428c to a valve open position shown in FIG. 43.

Following interconnection of syringe "NS" with connector 418 in the manner shown in FIG. 43, fluid can be forced from the syringe into a central fluid passageway 418a provided in connector 418. Fluid flowing through passageway 418a under pressure will cause valve member 430 to move away from valve seat 428c and into engagement with the inboard portion of member 428. When the vial is filled, valve member 430 will return to its closed position shown in FIG. 45.

After the vial has been filled with the selected fluid, cap 425 is pivoted downwardly relative to the outer casing and into a closed snapped position so as to maintain the interior of the vial in a sealed, aseptic and sterile condition. In its sealed, condition, the vial assembly can be stored as may be necessary until it is to be used to fill the reservoir of a fluid dispenser. A typical fluid dispenser, is shown in FIG. 45 and identified by the numeral 435. Dispenser 435 is provided with a vial receiving opening 435a which closely receives end portion 402b in the manner shown in FIG. 45. As before, dispenser 435 includes internally disposed tabs that matably engage locking tabs provided on casing 402 so that once the vial assembly is fully mated with the dispenser it cannot be removed.

As indicated in FIGS. 45 and 47, fluid dispenser 435 is provided proximate opening 435a with a valve opening member 437 which has a fluid passageway 437a. Member 437 is held in position by a support member 439 so that passageway 437a is in communication with a central passageway 409 defined by the interior wall of skirt portion 408c. Passageway 437a is, in turn, in communication with the fluid reservoirs of the dispenser.

When the vial assembly is mated with fluid dispenser 435, operating member 437 will urge cylindrical valve member 410 to the right, or inwardly toward vial chamber 104a, thereby opening the valve and permitting fluid flow from chamber 104a, between legs 437b provided on member 437 (FIG. 47), into passageway 437a and into the fluid reservoirs of dispenser 435.

FIGS. 48 through 51, illustrate alternate form of vial assembly of the present invention. The apparatus of this embodiment of the invention, which is generally designated by the numeral 450, is similar in many respects to that shown in FIGS. 41 through 47 except that fluid inlet and outlet valve means are of a slightly different construction. As before, the vial assembly includes a vial 104 having a fluid chamber 104a for containing the fluid to be added to the reservoir of a fluid dispenser or other fluid delivery device. Surrounding vial 104 is an outer casing 452 having end portions 452a and 452b. Because of the similarly of this embodiment to the embodiment just described, like numerals are used where appropriate to identify like components.

As best seen in FIG. 49, the fluid chamber of the vial of this latest embodiment of the invention is filled with fluid using a needleless syringe "S-1" having a tip 454 that is closely received within the syringe connector portion 456 of inlet fill valve assembly 458. In a manner presently to be described, as the fluid chamber is filled, a plunger assembly 460 is moved from the position shown in FIG. 48 to the position shown in FIG. 49 where it abuts a shoulder 462 formed on casing 452.

Plunger assembly 460 here comprises an elastomeric member 464 having a central passageway 464a and a plurality of circumferentially extending sealing beads 464b which sealably engage the inner wall 104d of vial 104. Mounted within passageway 464a is an outlet valve means which comprises a valve seat member 466 having a valve seat 466a and a ball-type valve member 468 which is movable toward and away from the valve seat in a manner presently to be described. Also comprising a part of the outlet valve means is a locking member 470 which is disposed within passageway 464a. Member 470 has a flange portion 470a which is received within an annular groove 464c provided member 460 (FIG. 48) and lockably engages an annular protuberance 466b which is formed on valve seat member 466 and which also extends into groove 464c. A skirt like portion 466c extends from protuberance 466b and an includes inboard edge 466d that sealably engages an elastomeric seal 472 carried by the fluid dispenser when the vial assembly is mated with the fluid dispenser in a manner presently to be described.

For filling the fluid chamber of the vial assembly, a syringe connector means is provided which includes the previously identified syringe connector portions 456 within which tip 454 of the syringe is telescopically received in the manner shown in FIG. 49. Connector portion 456 also comprises a part of the fill assembly 458 of this embodiment of the invention, which assembly further includes the inlet or fill valve means including a valve housing 477, as well as annular seal members 478 and 480 all of which are held in position within casing 452 by interconnection means comprising the previously identified crimp cap 150. The fill valve means of this latest form of the invention includes a valve seat member 484, the forward portion of which comprises the previously identified syringe connector portion 456. The rearward portion of member 484 includes a disk-like protuberance 484a and a skirt portion 484b that extends therefrom. Disposed interiorly of skirt portion 484b is a valve seat 484c.

A ball-type valve member 488, which also forms a part of the fill valve means, is movable within skirt portion 484b from a closed position wherein it sealably engages seat 484c to a valve open position shown in FIG. 48. Biasing means, here shown as a coil spring 490, continuously urges valve member 488 toward seat 484c. Valve seat member 484 can be constructed from any suitable plastic material such as polypropylene, polystyrene, or various types of acrylics. Valve member 488 can be constructed of similar plastic materials or can be constructed of metal, glass or various elastomers. Coil spring 480 can be constructed from appropriate metals or plastics.

Following interconnection syringe "S-1" with connector 456 in the manner shown in FIG. 49, fluid can be forced from the syringe into a central fluid passageway 456a provided in connector 456. Fluid flowing through passageway 456a under pressure will cause valve member 488 to move away from valve seat 484c against the urging of spring 490. When the vial is filled, spring 490 will urge valve member 488 to return to its closed substantially sealed position shown in FIG. 48.

After the vial has been filled with the selected fluid, cap 482 is theadably reconnected to the outer casing so as to maintain the interior of the vial in a sealed, aseptic condition. In its sealed, condition, the vial assembly can be stored as may be necessary until it is to be used to fill the reservoir of a selected fluid dispenser. The fluid dispenser, which is identified in FIG. 50 by the numeral 493, is provided with a vial receiving opening 493a which closely receives end portion 452b in the manner shown in FIG. 50. As before, dispenser 493 includes internally disposed tabs that matably engage locking tabs provided on casing 452 so that once the vial assembly is fully mated with the dispenser it cannot be removed.

As indicated in FIGS. 50 and 52, fluid dispenser 493 is provided proximate opening 493a with a valve opening member 495 which has a fluid passageway 495a. Member 495, which forms a part of a support member 496, is aligned with a central passageway 497 defined by the interior wall of skirt portion 466c.

When the vial assembly is mated with fluid dispenser 493 in the manner shown in FIG. 51, operating member 495 will enter passageway 497 and urge valve member 468 to the right, or inwardly toward vial chamber 104a against the urging of a biasing means or spring 498, thereby opening the valve and permitting fluid flow from chamber 104a, between legs 495b provided on member 495 (FIG. 52), into passageway 495a and into the fluid reservoirs of dispenser 493.

Turning next to FIGS. 53 through 57, still another alternate form of vial assembly of the present invention is there illustrated and generally identified by the numeral 500. The apparatus of this embodiment of the invention is similar in many respects to that shown in FIGS. 41 through 47, but includes fluid outlet valve means of a slightly different construction. As before, the vial assembly includes a vial 104 having a fluid chamber 104a for containing the fluid to be added to the reservoir of a fluid dispenser or other fluid delivery device. Surrounding vial 104 is an outer casing 402 having end portions 402a and 402b. Casing 402 is identical to that previously described save that end 402b is provided with threads 501, the purpose of this will later be described. Because of the similarly of this embodiment to those previously described, like numerals are used where appropriate to identify like components.

As was the case with the embodiment of the invention shown in FIGS. 41 through 47, the fluid chamber of the vial is filled with fluid using a needleless syringe "NS" having a conventional luer connector. In a manner presently to be described, as the fluid chamber is filled, a plunger assembly 504 is moved from the position shown in FIG. 54 toward the position shown in FIG. 55.

Plunger assembly 504 here comprises an elastomeric member 506 having a central passageway 506a, including an enlarged diameter portion 507, and a plurality of circumferentially extending sealing beads 506b which sealably engage the inner wall 104d of vial 104. Mounted within passageways 506a and 507 is an outlet valve means which here comprises an elastomeric valve member 508 having a peripheral bead 508a. In a manner presently to be described, valve member 508 is movable toward and away from a porous polymer housing 510 that is disposed within an enlarged diameter portion 507. Housing 510 includes a central cavity 510a which has the configuration of valve member 508 and is adapted to closely receive the valve member.

For filling the fluid chamber of the vial, a syringe connector means is provided in the form of a connector stem 418 that includes a luer type connector which is lockably received within the syringe receptacle in the manner shown in FIG. 43. Connector stem 418 comprises a part of the fill assembly 420 of this embodiment of the invention which assembly is identical to that shown in FIGS. 41 through 47 as previously described herein.

Following interconnection of syringe "NS" with connector 418 in the manner shown in FIG. 55, fluid can be forced from the syringe into a central fluid passageway 418a provided in connector 418. Fluid flowing through passageway 418a under pressure will cause valve member 430 to move away from valve seat 428c and into engagement with the inboard portion of member 428. When the vial is filled, valve member 430 will return to its closed position as shown in FIG. 56.

After the vial has been filled with the selected fluid, cap 425 is pivoted downwardly relative to the outer casing and into a locked position so as to maintain the interior of the vial in a sealed, aseptic condition. In its sealed, condition, the vial assembly can be stored as may be necessary until it is to be used to fill the reservoir of a fluid dispenser. The fluid dispenser, which is identified in FIG. 56 by the numeral 515, is provided with an internally threaded vial receiving opening 515a which closely receives threaded end portion 402b in the manner shown in FIG. 57. As previously mentioned, casing 402b includes external threads 501 that threadably engage internal threads 517 provided in vial receiving opening 515a of dispenser 515. Locking tabs "T" provided on casing 402 lockably engage tabs "T-1" provided on dispenser 515 (FIG. 56).

As indicated in FIGS. 57 and 58, fluid dispenser 515 is provided proximate opening 515a with a valve opening member 519 which has a fluid passageway 521. Member 519 includes a valve member engaging element 523 that engages valve member 508 and urges it into cavity 510a provided in porous member 510 when the vial assembly is mated with the fluid dispenser in the manner shown in FIG. 57. Upon valve member 508 seating within cavity 510a fluid will flow from chamber 104a, through porous member 510 into passageway 521 and then into the fluid reservoirs of dispenser 515. (See the flow arrows of FIG. 57.)

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid container assembly for use with a fluid delivery apparatus of the character having a base and a stored energy means for forming in conjunction with the base a fluid reservoir having an inlet and an outlet, said stored energy means being adapted to expel fluid from the fluid reservoir, said fluid container assembly comprising:

(a) a container having a fluid chamber having an inlet and an outlet;

(b) a plunger telescopically movable within said fluid chamber of said container as a result of fluid pressure being exerted thereon by fluid introduced through said inlet; and (c) inlet valve means disposed between said plunger and said inlet for controlling fluid flow into said chamber, said inlet valve means including a valve member movable in response to fluid pressure from a first valve closed position to a second valve open position.

2. A fluid container assembly as defined in claim 1 in which said plunger includes a frangible portion pierceable by a cannula.

3. A fluid container assembly as defined in claim 1 further including outlet valve means for controlling fluid flow through said outlet of said fluid chamber.

4. A fluid container assembly as defined in claim 3 in which said outlet valve means comprises a valve carried by said plunger.

5. A fluid container assembly for use with syringe having a cannula, said container assembly comprising:

(a) a container including a fluid chamber having an inlet, an outlet, and an inner surface;

(b) covering means for covering said inner surface;

(c) sealing means for sealably closing said inlet of said fluid chamber of said container, said sealing means including inlet valve means for controlling fluid flow into said fluid chamber;

(d) a plunger telescopically movable within said container by fluid pressure from a first location proximate said sealing means to a second, spaced-apart location; and (e) an outer casing surrounding said container, said casing having first and second ends, one of said first and second ends being closed by a removable closure cap and the other of said first and second ends being closed by a closure assembly, said closure assembly comprising vent means for venting gases contained within said fluid chamber to atmosphere.

6. An apparatus as defined in claim 5 in which said covering means comprises a plurality of layers of material which cooperate to form a barrier between said inner surface of said fluid chamber and fluid contained within said chamber.

7. A fluid container assembly for use with a syringe having a cannula, said container assembly comprising:
   (a) a container having a fluid chamber having a fluid inlet and a fluid outlet;
   (b) sealing means for sealably closing said fluid inlet of said fluid chamber of said container;
   (c) a plunger telescopically movable within said container by fluid pressure from a first location proximate said sealing means to a second, spaced-apart location; and
   (d) outlet valve means for controlling fluid flow through said fluid outlet of said fluid chamber, said outlet valve means comprising a duck-bill type valve member integrally formed with said plunger.

8. A fluid container as defined in claim 7 in which said sealing means includes a frangible portion pierceable by the cannula of the syringe.

9. A fluid container as defined in claim 7 in which said sealing means includes an inlet valve means for controlling fluid flow into said fluid chamber.

10. A fluid container assembly for use with a syringe having a cannula, said container assembly comprising:
    (a) a container having a fluid chamber having a fluid inlet and a fluid outlet;
    (b) sealing means for sealably closing said fluid inlet of said fluid chamber of said container;
    (c) a plunger telescopically movable within said container by fluid pressure from a first location proximate said sealing means to a second, spaced-apart location;
    (d) outlet valve means for controlling fluid flow through said fluid outlet of said fluid chamber, said outlet valve means comprising a ball type valve member carried by said plunger for movement relative thereto between a valve closed position and a valve open position.

11. A fluid container as defined in claim 10 further including a porous member carried by said plunger, said porous member having a cavity adapted to receive said valve member.

12. A fluid container assembly for use with a syringe having a cannula, said container assembly comprising:
    (a) a container having a fluid chamber having a fluid inlet and a fluid outlet;
    (b) sealing means for sealably closing said fluid inlet of said fluid chamber of said container, said sealing means including inlet valve means for controlling fluid flow into said fluid chamber, said inlet valve means including a valve member movable in response to fluid pressure from a first valve closed position to a second valve open position;
    (c) a plunger telescopically movable within said container by fluid pressure from a first location proximate said sealing means to a second, spaced-apart location; and
    (d) outlet valve means for controlling fluid flow through said fluid outlet of said fluid chamber.

13. A fluid container as defined in claim 12 in which said outlet valve means comprises a valve member carried by said plunger for movement relative thereto between a valve closed position and a valve open position.

14. A fluid container as defined in claim 12 in which said sealing means includes syringe connector means for connecting the syringe, said syringe connector means comprising a connector stem provided with a luer type connector for interconnection with the syringe.

\* \* \* \* \*